United States Patent [19]

Bakshi et al.

[11] Patent Number: 5,527,807
[45] Date of Patent: Jun. 18, 1996

[54] 7β-SUBSTITUTED-4-AZA-5α-CHOLESTAN-3-ONES AS 5α-REDUCTASE INHIBITORS USEFUL IN THE PREVENTION AND TREATMENT OF HYPERANDROGENETIC DISORDERS

[75] Inventors: Raman K. Bakshi, Edison; Gary H. Rasmusson, Watchung; Richard L. Tolman, Warren; Gool F. Patel, Millington; Georgianna Harris, Tinton Falls, all of N.J.

[73] Assignee: Merck & Co., Inc., Rahway, N.J.

[21] Appl. No.: 335,861

[22] Filed: Nov. 15, 1994

Related U.S. Application Data

[63] Continuation-in-part of Ser. No. 886,023, filed as PCT/US93/04615, May 14, 1993, publishced as WO93/23419, Nov. 25, 1993, abandoned.

[51] Int. Cl.$^6$ ............................................ A61K 31/58
[52] U.S. Cl. .................................. 514/284; 546/77
[58] Field of Search ..................... 546/77, 78; 514/284

[56] References Cited

U.S. PATENT DOCUMENTS

| | | | |
|---|---|---|---|
| 2,227,876 | 1/1941 | Bolt | 546/77 |
| 3,239,417 | 3/1966 | DiTullio et al. | 546/77 |
| 3,264,301 | 8/1966 | Doorenboos | 546/77 |
| 3,285,918 | 11/1966 | Doorenboos et al. | |
| 4,220,775 | 9/1980 | Rasmusson et al. | 546/77 |
| 4,317,817 | 3/1982 | Blohm et al. | |
| 4,377,584 | 3/1983 | Rasmusson et al. | 546/77 |
| 4,596,812 | 6/1986 | Chidsey, III et al. | 514/256 |
| 4,732,897 | 3/1988 | Cainelli et al. | 546/77 |
| 4,760,071 | 7/1988 | Rasmusson et al. | 546/77 |
| 4,845,104 | 7/1989 | Carlin et al. | 546/77 |
| 4,859,681 | 8/1989 | Rasmusson et al. | 546/77 |
| 4,882,319 | 11/1989 | Holt et al. | 546/77 |
| 4,888,336 | 12/1989 | Holt et al. | 546/77 |
| 4,910,226 | 3/1990 | Holt et al. | 514/178 |
| 5,049,562 | 9/1991 | Rasmusson et al. | 546/77 |
| 5,120,742 | 6/1992 | Rasmusson et al. | 514/284 |
| 5,175,155 | 12/1992 | Juniewicz et al. | 514/284 |
| 5,237,064 | 8/1993 | Bakshi et al. | 546/77 |
| 5,359,071 | 10/1994 | Durette et al. | 546/77 |

FOREIGN PATENT DOCUMENTS

| | | |
|---|---|---|
| 970692 | 7/1975 | Canada ........................ 546/77 |
| 0004949 | 10/1979 | European Pat. Off. . |
| 0155096 | 9/1985 | European Pat. Off. . |
| 0200859 | 11/1986 | European Pat. Off. . |
| 0277002 | 6/1988 | European Pat. Off. . |
| 0289327 | 11/1988 | European Pat. Off. . |
| 0314199 | 5/1989 | European Pat. Off. . |
| 0343954 | 11/1989 | European Pat. Off. . |
| 0375349 | 6/1990 | European Pat. Off. . |
| 0375347 | 6/1990 | European Pat. Off. . |
| 0375345 | 6/1990 | European Pat. Off. . |
| 0375344 | 6/1990 | European Pat. Off. . |
| 1465544 | 11/1965 | France . |
| WO91/12261 | 2/1990 | WIPO . |
| WO91/13550 | 9/1991 | WIPO . |
| WO92/07586 | 5/1992 | WIPO . |
| WO92/16233 | 10/1992 | WIPO . |
| WO93/23419 | 11/1993 | WIPO . |

OTHER PUBLICATIONS

Geldof et al., Abstract: Eur. J. Cancer, vol. 26, "Enzyme Inhibitors in Hormone Dependent Prostate Cancer Treatment", p. 188 (1990).

Kedderis et al., Toxicology and Applied Pharmacology, vol. 93, (1988), "Studies with Nitrogen–Containing Steroids and Freshly Isolated Rat Hepatocytes: Role of Cytochrome P–450 in Detoxication", pp. 403–412.

Kedderis et al., Toxicology and Applied Pharmacology, vol. 103, (1990), "The Role of Metabolism and Covalent Binding in the Cytotoxicity of a Nitrogen–Containing Steroid toward Rat Hepatocytes", pp. 222–227.

Endo., vol. 91, No. 2, pp. 427–437 (1972) by Neri, et al., "A Biological Profile of a Non–steroida Antiandrogen, SOH 13521 . . . ".

Steroids, 14, 269–283(1969), by Nayfeh, et al., "Metabolism of Progesterone by Rat Testicular Homogenates".

Endo., vol. 92, pp. 1216–1222 (1973) by Voight & Hsia.

J. Pharm. Sci., 62, No. 4, pp. 638–640 (1973) by Doorenbos & Solomons, "Synthesis & Antimicrobial Properties of 17 Beta–Isopentyloxy–4–Aza–5–Alpha–Androstane and the 4–Methyl Derivative".

J. Pharm. Sci., 60, No. 8, pp. 1234–1235 (1971) by Doorenbos & Brown, "4,17 Alpha–Dimethyl–4–Aza–5 Alpha–Androstane–17 beta–ol Acetate & Related Azasteroids".

J. Pharm., 63, No. 4, pp. 620–622 (1974) by Doorenbos & Kim, "Synthesis & Evaluation of Antimicrobial Properties of Amidinoazaandrostanes and Guanidinoazaandrostanes".

J. Med. Chem. (1986) 29 (11): pp. 2298–3115 by Rasmusson, et al., "Aza Steroids, Structure–Activity Relationships".

Prostate (1986) 9(1): pp. 65–75 by Brooks, et al., "Prostatic Effects Induced in Dogs By . . . 5 alpha–Reductase Inhibitors".

Steroids (1986) 47 (1): pp. 1–19 by Brooks, et al., "5 Alpha–Reductase Inhibitory . . . Activities of Some 4–Aza-–Steroids in the rat".

Endocr. (1985) 117 (2): pp. 571–579, by Liang, et al., "Species Differences in Prostatic Steroidal 5 Alpha–Reductases of Rat, Dog and Human".

J. Med. Chem. (1984) 27 (12) : pp. 1690–1701, by Rasmusson, et al., "Azasteroids as Inhibitors of Rat Prostatic 5 alpha–reductase".

J. Org. Chem. (1981) vol. 46, No. 7, pp. 1442–1446, T. Back, et al., "N–Chloroazasteroids . . . ".

Chem. Abstracts, vol. 95, 109055, by T. Liang, et al. "Inhibition of 5 Alpha–Receptor Binding . . . by a 4–Methyl–4–aza–Steroid"(1981).

JNCI, vol. 74, No. 2, pp. 475–481 (Feb. 1985), by N. Kadohama, et al., "Retardation of Prostate Tumor Progression in the Noble Rat by 4–Methyl–4–Aza–Steroidal Inhibitors of 5 Alpha–Reductase".

(List continued on next page.)

Primary Examiner—Donald G. Daus
Attorney, Agent, or Firm—Joanne M. Giesser; Catherine D. Fitch

[57] ABSTRACT

Described are new 7β-substituted 4-aza-5α-cholestan-3-ones and related compounds as 5α-reductase inhibitors.

8 Claims, No Drawings

OTHER PUBLICATIONS

The Prostate, vol. 10, pp. 189–197 (1987) by G. Andriole, et al., "The Effect of 4MA . . . on the Growth of . . . Human Tumors . . . ".

J. Endocr., vol. 57, pp. 111–121 (1973) by K. D. Bingham, et al., "The Metabolism of Testosterone by Human Male Scalp Skin".

Bioinorganic Chemistry, 17, pp. 372–376 (1986) by B. W. Metcalf, et al., "Patent Inhibition of Human Steroid . . . by 3–Androstene–3–Carboxylic Acid".

Biochemistry, 1990, vol. 29, pp. 2815–2824, by M. A. Levy, et al., "Inhibition of Rat Liver Steroid 5 Alpha–Reductase".

J. Med. Chem., 1990, vol. 33, pp. 943–950, by D. A. Holt, et al. "Steroidal A Ring Carboyxlic Acids . . . ".

J. Steroid Biochem., vol. 34, Nos. 1–6, pp. 571–575 (1989), by M. A. Levy, et al., "Interaction Between Rat Prostatic 5 Alpha–Reductase . . . ".

J. Med. Chem., vol. 33, pp. 937–942 (1990) by D. A. Holt, et al., "Steroidal A Ring Aryl Carboxylic Acids".

TIPS, Dec. 1989, vol. 10, pp. 491–495, by D. W. Metcalf, et al., "Inhibitors of . . . 5 Alpha–Reductase in Benign Prostatic Hyperplasia . . . ".

Steroids, vol. 35, No. 3 (Mar. 1980) pp. 1–7, by L. Murphy, et al., "Effect of Estradiol on a . . . Binding Protein in the Uterus of the Mouse".

Prostate, vol. 9, pp. 311–318 (1986) by N. Stone, et al., "Estrogen Formation in Human Prostatic Tissue . . . ".

Steroids, vol. 47, No. 1, pp. 1–19 (1986) by J. R. Brooks, et al., "5 Alpha–Reductase Inhibitory . . . Activities of Some 4–Azasteroids . . . ".

Lancet, No. 1986, No. 8515, pp. 1095–1096, by F. Labrie, et al. "Combination therapy in prostate cancer".

J. Clin. Endocrin. and Metabl., vol. 55, No. 1, pp. 188–193 (1987), by R. Rittmaster, et al., "The Effects of . . . a 5 Alpha–Reductase Inhibitor . . . ".

J. Clin. Endocrin and Metab., vol. 74, No. 2, pp. 345–350 (1990), by A. Diani, et al., "Hair Growth Effects of Oral Administration of Finasteride . . . ".

J. Clin. Endocrinol. Metab. 67, No. 4, pp. 808–816 (1988), by N. Bruchovsky, et al., "Kinetic Parameters of 5 Alpha–Reductase Activity in Stroma & Epithelium of Normal Hyperplastic & Carcinomatous Human Prostates".

J. Steroid Biochem. 26 (3) pp. 349–353 (1987), by R. Hudson, "Comparison of Nuclear 5 Alpha–Reductase Activities in the Stromal and Epithelial Fractions of Human Prostatic Tissue".

J. Biol. Chem. 251 (19) pp. 5895–5900 (1976), by R. J. Moore, et al., "Steroid 5 Alpha–Reductase in Cultured Human Fibroblasts".

J. Biol. Chem. 264 (27) pp. 16249–16255 (1989), by S. Andersson, et al., "Expression Cloning & Regulation of steroid 5 alpha–Reductase and Exzyme Essential for Male Sexual Differentiation".

Proc. Nat'l Acad Science 87, pp. 3640–3644 (1990), by S. Andersson, et al., "Structural & Biochemical Properties of cloned and expressed human and rat steroid 5 alpha–reductases".

Nature 354, pp. 159–161 (Nov. 14, 1991), by S. Andersson, et al., "Deletion of Steroid 5 Alpha–Reductase–2 Gene in Male Pseudohermaphroditism".

Biol of Reproduction vol. 45, pp. 168–173 (1992), by J. D. Wilson, "Syndromes of Androgen Resistance".

J. Cancer Res. Clin. Oncol. 118, pp. 50–55 (1992), by A. Geldof, et al., "Consideration of the Use of . . . 4MA . . . in Prostate Cancer Therapy".

The Prostate 18, pp. 215–227 (1991), by J. Brooks, et al., "Effect of Castration, DES, Flutamide, and MK–906 on Growth of the Dunning Rat Prostatic Carcinoma . . . ".

Eur. J. Pharm. 183 (5), p. 1757 (1990), by Y. Masubuchi, et al., "Lack of DHT Inhibition . . . by Treatment of 4MA . . . ".

Stinson, Chem. Eng. News, Jun. 29, 1992, pp. 7–8.

Helliker, Wall Street Jour., Jun. 7, 1991, pp. A1 and A7 (1991).

Diani, et al, Jour. of Clin & Metab., vol. 74, pp. 345–350, (1992).

Back, et al, Jour. Org. Chem., vol. 54, pp. 1904–1910 (1992).

Back, et al, Can. Jour. of Chem., vol. 69, No. 9, pp. 1482–1486 (1991).

Suddoth et al., Pharmacotherapy, vol. 13, No. 4, pp. 309–329 (1993), "Finasteride: The First 5–alpha Reductase Inhibitor".

Rhodes et al., "Effects of 1 Year Treatment with Oral MK386, an Inhibitor of Type 1 5Alpha–Reductase, in the Stumptailed Macaque (*Macaca arctoides*)", presented at Society for Investigative Dermatology Meeting, Chicago, Illinois, May 24–28, 1995.

ps
7β-SUBSTITUTED-4-AZA-5α-CHOLESTAN-3-ONES AS 5α-REDUCTASE INHIBITORS USEFUL IN THE PREVENTION AND TREATMENT OF HYPERANDROGENETIC DISORDERS

CROSS-REFERENCE TO RELATED APPLICATIONS

This application is a continuation in part of application Ser. No. 886023, filed as PCT/US93/04615, May 14, 1993, published as WO93/23419, Nov. 25, 1993, now abandoned.

BACKGROUND OF THE INVENTION

The present invention is directed to new 7β-substituted-4-aza-5α-cholestan-3-ones and related compounds and the use of such compounds as 5α-reductase inhibitors.

DESCRIPTION OF THE PRIOR ART

The art reveals that certain undesirable physiological manifestations, such as acne vulgaris, seborrhea, female hirsutism, male pattern baldness and benign prostatic hypertrophy, are the result of hyperandrogenetic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It is now known in the art that the principal mediator of androgenic activity in some target organs is 5α-dihydrotestosterone, and that it is formed locally in the target organ by the action of testosterone-5a-reductase. It is also known that inhibitors of testosterone-5a-reductase will serve to prevent or lessen symptoms of hyperandrogenic stimulation.

A number of 4-aza steroid compounds are known in the art as 5α-reductase inhibitors. For example, See U.S. Pat. Nos. 2,227,876, 3,239,417, 3,264,301 and 3,285,918; French Patent No. 1,465,544; Doorenbos and Solomons, J. Pharm. Sci. 62, 4, pp. 638–40 (1973); Doorenbos and Brown, J. Pharm. Sci., 60, 8, pp. 1234–1235 (1971); and Doorenbos and Kim, J. Pharm. Sci. 63, 4, pp. 620–622 (1974).

In addition, U.S. Patent Nos. 4,377,584, 4,220,775, 4,859,681, 4,760,071 and the articles J. Med. Chem. 27, p. 1690–1701 (1984) and J. Med. Chem. 29, 2998–2315 (1986) of Rasmusson, et al., U.S. Pat. No. 4,845,104 to Carlin, et al., and U.S. Pat. No. 4,732,897 to Cainelli, et al. describe 4-aza-17β-substituted- 5α-androstan-3-ones which are said to be useful in the treatment of DHT-related hyperandrogenic conditions.

However, despite the suggestion in the prior art that hyperandrogenetic diseases are the result of a single 5α-reductase, there are reports regarding the presence of other 5α-reductase isozymes in both rats and humans. For example, in human prostate, Bruchovsky, et al. (See J. Clin. Endocrinol. Metab. 67, 806–816, 1988) and Hudson (see J. Steroid Biochem. 26, p 349–353, 1987) found different 5α-reductase activities in the stromal and epithelial fractions. Additionally, Moore and Wilson described two distinct human reductases with peaks of activities at either pH 5.5 or pH 7–9. (See J. Biol. Chem. 251, 19, p. 5895–5900, 1976.)

Recently, Andersson and Russell isolated a cDNA which encodes a rat liver 5α-reductase (see J. Biol. Chem. 264 pp. 16249–55 (1989). They found a single mRNA which encodes both the liver and prostatic reductases of rats. The sequence of this rat gene was later used to select a human prostatic cDNA encoding a 5α-reductase termed "5α-reductase 1". (See Proc. Nat'l. Acad. Sci. 87, p. 3640–3644, 1990.)

More recently, a second, human prostatic reductase (5α-reductase 2) has been cloned with properties identified with the more abundant form found in crude human prostatic extracts. (See Nature, 354, p. 159–161, 1991.)

Further, "Syndromes of Androgen Resistance"—The Biology of Reproduction, Vol. 46, p. 168–173 (1992) by Jean O. Wilson indicates that the 5α-reductase 1 enzyme may be associated with hair follicles.

Thus, the art supports the existence of at least two genes for 5α-reductase and two distinct isozymes of 5α-reductase in humans. Both forms are present in prostatic tissue in which, 5α-reductase 2, is the more abundant, and the other isozyme, 5α-reductase 1, is believed to be more abundant in scalp tissue.

In the treatment of hyperandrogenetic disease conditions, e.g. benign prostatic hyperplasia (BPH), it would be desirable to have one drug entity which is active against both enzymes 1 and 2 in the prostate to substantially inhibit dihydrotesterone (DHT) production. Alternatively, it would be desirable to have a drug entity which is highly selective for inhibiting the scalp associated enzyme 5α-reductase 1, for use in treating diseases of the skin and scalp, e.g. acne and alopecia. This latter drug could also be used in combination with PROSCAR® (finasteride) which is highly selective for the prostatic enzyme 5α-reductase 2 for combination therapy in the treatment of BPH.

SUMMARY OF THE INVENTION

The present invention discloses novel 7β-substituted-4-aza-5α-cholestan-3-one compounds which are useful for inhibiting the steroid 5α-reductase isozymes 1 and 2 and are particularly effective in selectively inhibiting the 5α-reductase 1 associated with the scalp and dually inhibiting both isozymes 1 and 2 in the oral, parenteral or topical treatment of benign prostatic hyperplasia, acne, female hirsutism, male pattern baldness, androgenic alopecia, prostatitis, and the prevention and treatment of prostatic carcinoma.

In accordance with the present invention there is provided novel 7β-substituted-4-aza-5a-cholestan- 3-one compounds of the formula:

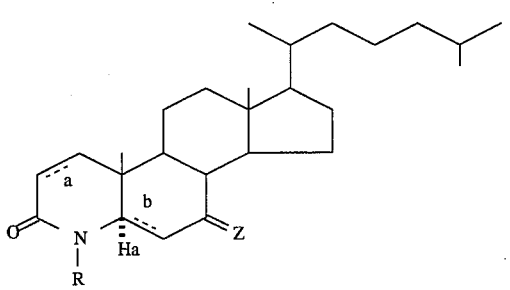

wherein

R is selected from hydrogen, methyl or ethyl; the dashed lines a and b, indicate double bonds which can be present providing that when b is present, the 5α hydrogen, Ha is absent;

Z can be
1) oxo,
2) α-hydrogen and a β-substituent selected from: $C_1$–$C_4$ alkyl, $C_2$–$C_4$ alkenyl, $CH_2COOH$, hydroxy, allyl, carboxy, $COOC_1$–$C_4$ alkyl esters; $OCONR^1R^2$, where $R^1$ and $R^2$ are independently H, $C_1$–$C_4$ alkyl, phenyl, benzyl, and $R^1$ and $R^2$ together with the nitrogen can form a 5–6 membered saturated heterocyclic ring, optionally with one other heteroatom; $OC_1$–$C_4$ alkyl, $OC_3$–$C_6$ cycloalkyl, —$OCOCH_3$, halo, hydroxy $C_1$–$C_2$ alkyl, halo $C_1$–$C_2$ alkyl or trifluoromethyl, $C_3$–$C_6$ cycloalkyl;
3) =CH—R' where R' is H, $C_1$–$C_4$ alkyl;
4) spiro:

where R' is H, $C_1$–$C_4$ alkyl;
and stereoisomers and pharmaceutically acceptable salts and esters thereof.

Also disclosed are processes for their preparation, pharmaceutical formulations comprising the novel compounds as active ingredients and methods of inhibiting prostatic and scalp 5α-reductases in diseases which occur under hyperandrogenic conditions, e.g. benign prostatic hyperplasia, with the novel compounds and their pharmaceutical formulations.

The 17-substituent cholestane side chain is in the beta configuration.

DETAILED DESCRIPTION OF THE INVENTION AND PREFERRED EMBODIMENTS

By the term "$C_1$–$C_4$ alkyl" as used herein, is meant to include: e.g. methyl, ethyl, propyl, isopropyl, n-butyl, sec-butyl, isobutyl and t-butyl.

By the term "$C_2$–$C_4$ alkenyl" as used herein is meant to include vinyl, allyl, 1-propen-1-yl, 1-propen-2-yl, 1-buten-1-yl, 1-buten-2-yl, and the like.

By the term "$C_3$–$C_6$ cycloalkyl" as used herein is meant to include cyclopropyl, cyclobutyl, cyclopentyl, cyclohexyl.

By the term "halo" as used herein is meant to include fluoro, chloro, bromo, iodo.

By the term "$OC_1$–$C_4$ alkyl" as used herein is meant to include methoxy, ethoxy, propoxy, isopropoxy, n-butoxy, isobutoxy, sec-butoxy, t-butoxy.

By the term "$OC_3$–$C_6$ cycloalkyl" as used herein is meant to include: cyclopropyloxy, cyclobutyloxy, cyclopentyloxy, cyclohexyloxy.

Representative examples of Z are where α-substituent (dashed lines) is hydrogen and the beta substituent (wedge) is e.g. methyl, ethyl, propyl, allyl, carboxymethyl, hydroxy, methoxy, ethoxy, cyclopropyloxy, cyclopentyloxy, acetoxy, fluoro, chloro, bromo, trifluoromethyl, trichloromethyl, fluoromethyl, chloromethyl, carboxy, N N-dimethylcarbamate, hydroxymethyl, methoxymethyl, and the like.

Representative examples where Z is an alkenyl substituent, =CH—R', includes, e.g. =$CH_2$, =CH—$CH_3$, =CH—$CH_2CH_3$, and the like.

Representative examples where $R^1$, $R^2$ and the N can form a heterocyclic ring include:

N-morpholinyl, N-(4-methyl)piperazinyl, N-piperidinyl, and the like.

Representative examples where Z is the spiro substituent:

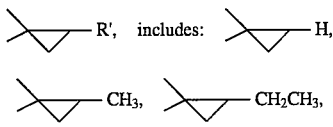

stereoisomers thereof and the like.

Representative compounds included in the invention wherein all of the 17- and 7-substituents are in the beta configuration are:

7-ethyl-4-methyl-4-aza-cholest-5-en-3-one
7-ethyl-4-methyl-4-aza-cholestane-3-one
7-ethyl-4-aza-cholest-5-en-3-one
7-ethyl-4-aza-5α-cholestan-3-one
7-carboxymethyl-4-aza-cholest-5-en-3-one
7-carboxymethyl-4-aza-cholestan-3-one
7-propyl-4-methyl-4-aza-cholest-5-en-3-one
7-propyl-4-methyl-4-aza-5α-cholestan-3-one
7-propyl-4-aza-cholest-5-en-3-one
7-propyl-4-aza-5α-cholestan-3-one
7-methyl-4-aza-cholest-5-en-3-one
7-methyl-4-aza-cholestan-3-one
4,7-dimethyl-4-aza-cholest-5-en-3-one
4,7-dimethyl-4-aza-5α-cholestan-3-one
4,7-dimethyl-4-aza-5α-cholestan-3,7-dione,
7-acetoxy-4-methyl-4-aza-5α-cholestan-3-one
4-methyl-4-aza-cholest-5-en-3,7-dione
7-hydroxy-4-methyl-4-aza-5α-cholestane-3-one
7-methoxy-4-methyl-4-aza-5α-cholestane-3-one
7-hydroxymethyl-4-aza-5α-cholestane-3-one
7-bromomethyl-4-aza-5α-cholestane-3-one
7-chloromethyl-4-aza-5α-cholestane-3-one
7-fluoromethyl-4-aza-5α-cholestane-3-one
7-carboxy-4-aza-5α-cholestane-3-one
7-trifluoromethyl-4-aza-cholest-5-en-3-one
4-methyl-4-aza-cholesta-3,7-dione
7,7-dimethoxy-4-methyl-4-aza-5α-cholestane-3-one
7-methoxy-4-methyl-4-aza-cholesta-5-en-3-one
7-methoxy-4-methyl-4-aza-cholesta-6-en-3-one
7-cyclopropyloxy-4-methyl-4-aza-5α-cholestane-3-one
7-cyclopropyloxy-4-methyl-4-aza-cholesta-5,7-dien-3-one
7-propylidene-4-methyl-4-aza-5α-cholestane-3-one
7-(2-ethyl)spiroethylene-4-methyl-4-aza-5α-cholestane-3-one
7-methyl-5-oxo-A-nor-3,5-seco-cholestanoic acid
7-ethyl-5-oxo-A-nor-3,5-seco-cholestanoic acid
7-propyl-5-oxo-A-nor-3,5-seco-cholestanoic acid
7-n-butyl-5-oxo-A-nor-3,5-seco-cholestanoic acid 7-t-butyl-5-oxo-A-nor-3,5-seco-cholestanoic acid
7-n-pentyl-5-oxo-A-nor-3,5-seco-cholestanoic acid
7-n-hexyl-5-oxo-A-nor-3,5-seco-cholestanoic acid.
The compounds of this invention can be made by procedures outlined in the following Flowsheets:
GENERAL FLOWSHEET
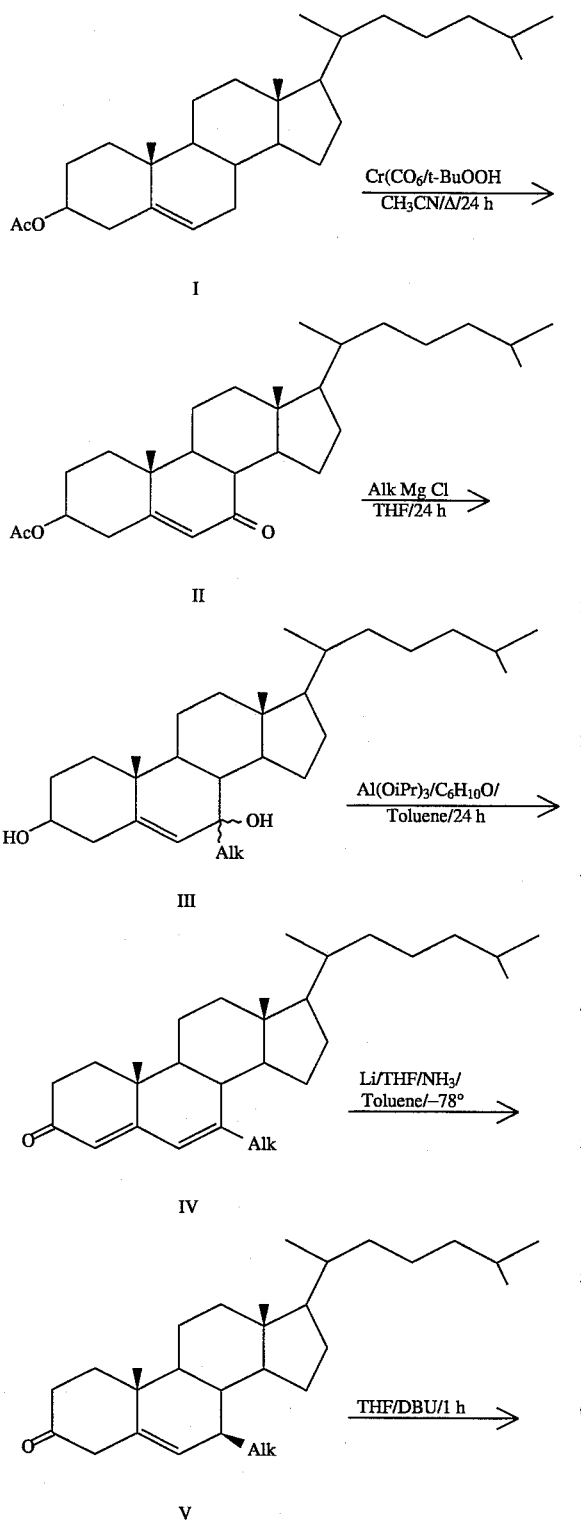
-continued
GENERAL FLOWSHEET
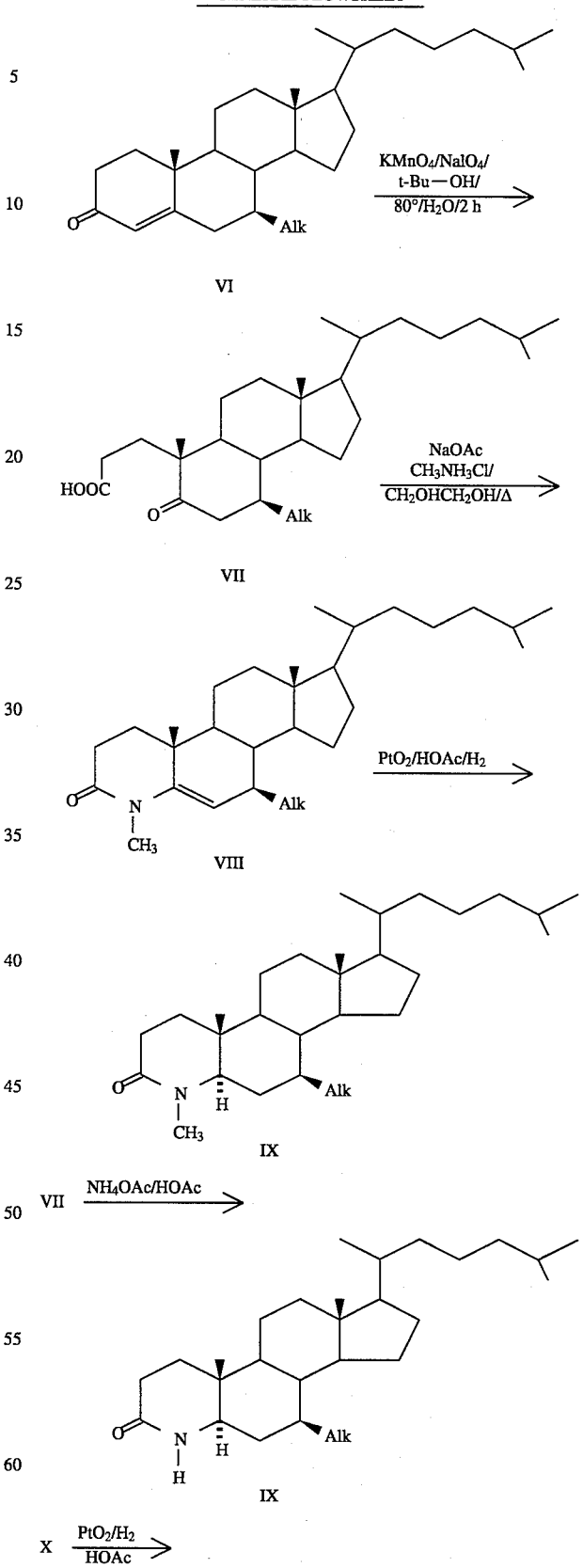

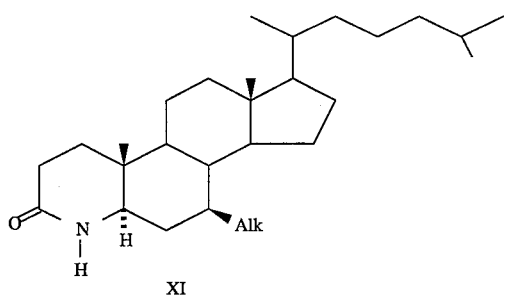

7-Beta Alkyl Series

The compounds of the instant invention comprising Z as a 7β alkyl group, e.g. methyl, ethyl, isopropyl, allyl, can be prepared by the procedure outlined in The General Flowsheet.

As seen in the Flowsheet, the starting 3-acetoxy-cholest-5-ene I (see Example 1 for synthesis) is oxidized to the corresponding 5-en-7-one II by treatment with hydrogen t-butyl peroxide and chromium hexacarbonyl in e.g. acetonitrile, at reflux. The $C_1$–$C_4$ alkyl group, designated Alk, e.g. methyl, can be introduced at this point by a Grignard reaction using e.g., alkyl magnesium chloride in e.g., anhydrous THF at 0°–23° C. to produce the 7-alkyl-7-hydroxy adduct III. This is then oxidized with e.g. aluminum isopropoxide and cyclohexanone (Oppenauer oxidation conditions) in refluxing toluene solvent to produce the 7-alkyl-4, 6-dien-3-one IV. This in turn is reduced via a e.g., metal-ammonia reduction, using lithium, liquid ammonia, THF and toluene at −78° C., quenching the reaction with dibromoethane and ammonium chloride, to selectively yield the 7-beta-alkyl-5-en-3-one V. In the next step the delta-5 double bond is isomerized to the 4-ene by use of DBU (1,8-diazabicyclo[5.4.0]undec-7-ene) in, e.g. refluxing tetrahydrofuran (THF) to produce the 7-beta-alkyl 4-en-3-one, VI. The A Ring is next cleaved by treatment with e.g. potassium permanganate, sodium periodate in t-butyl alcohol at 80° C. to produce the corresponding seco-acid VII. Treatment of the seco-acid with an appropriate amine e.g., methylamine hydrochloride and sodium acetate in ethylene glycol at 180° C., yields e.g., the 4-methyl4-aza-cholest-5-en-3-one VIII. This in turn is selectively reduced with e.g., $PtO_2$ catalyst in a hydrogen atmosphere, to remove the 5-position double bond to produce the 5α-hydrogen compound IX. The seco-acid VII can be similarly treated with ammonium acetate in acetic acid to produce the corresponding N-H compound, X, which can then be analogously treated with $PtO_2$ in a catalytic hydrogenation to produce the corresponding 5α-4N-H compound XI. Similarly, use of hydroxylamine or hydrazine for ring A closure of the seco acid will afford the corresponding delta-5-4N-X compounds where —X can be —OH or —$NH_2$, respectively. Reaction of the anion of saturated 4N-compound (generated from the NH precursor by NaH treatment) with methylsulfenyl chloride can provide the corresponding 4N—X compound where —X is —$SCH_3$. Thus, R can also be OH, —OH, —$NH_2$ or $SCH_3$ in the Formula.

FLOWSHEET A

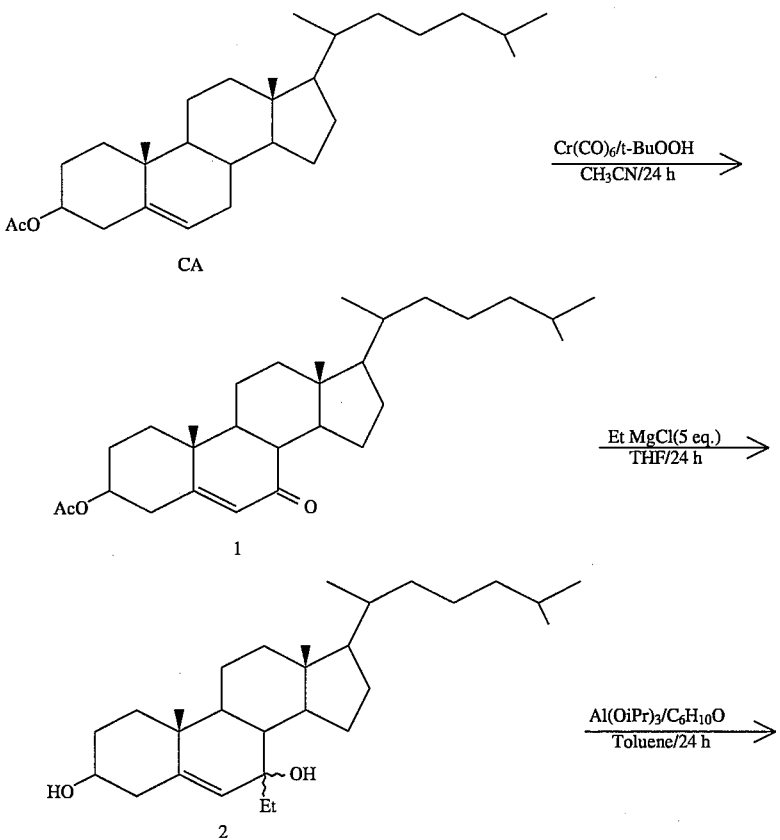

-continued
FLOWSHEET A
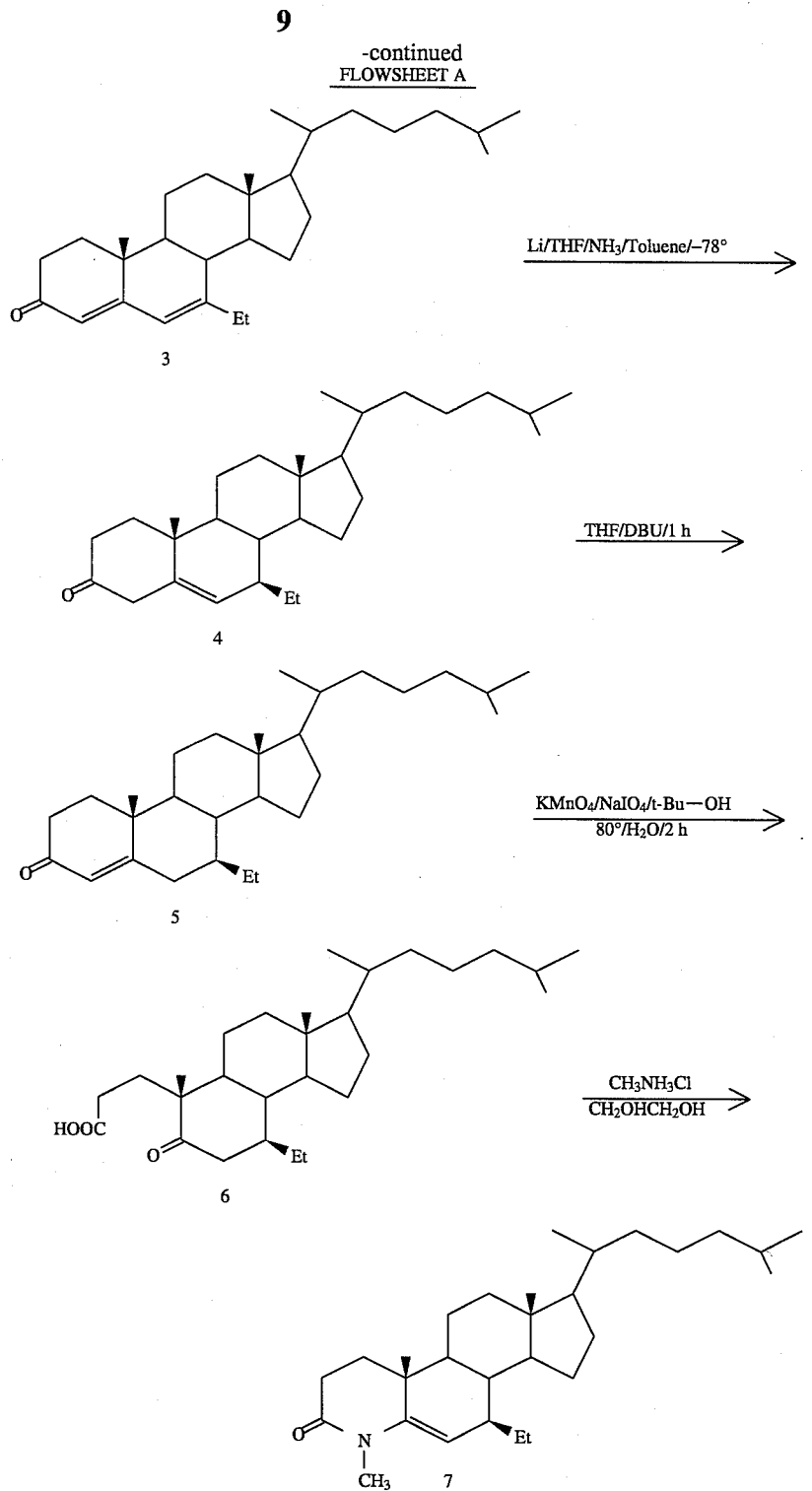

FLOWSHEET B

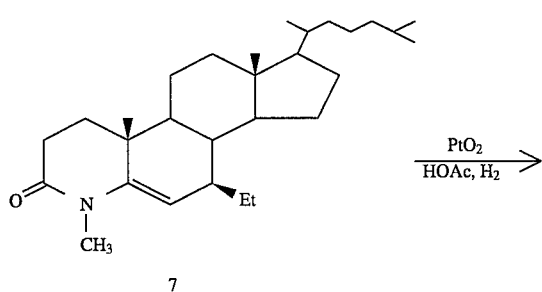

7

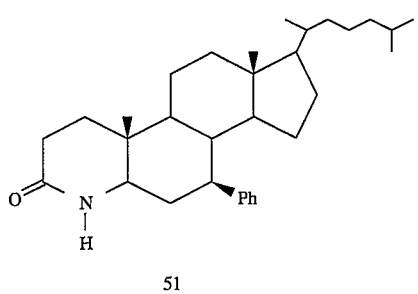

51

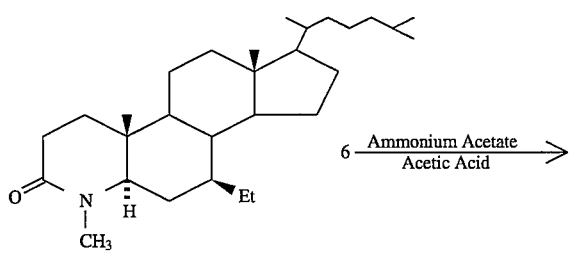

8

7-Beta-Ethyl-Cholestane Analogues

The 7-ethyl substituent is introduced into the cholestane series as illustrated in Flowsheets C and D by the same analogous procedure as described in the General Flowsheets.

The starting cholesteryl acetate CA is available commercially (Aldrich). This is treated using the analogous chromium hexacarbonyl/hydrogen t-butylperoxide/acetonitrile oxidation procedure (described in JCS Perkin Trans. 1985, p. 267 by A. J. Pearson) to yield the 3-acetoxy-cholest-5-en-7-one 1. This can be reacted with an alkyl Grignard reagent, e.g. ethyl magnesium chloride to form the adduct 2. This is oxidized under Oppenauer conditions to yield the dienone 3, which then can undergo metal-ammonia reduction to yield the 7β-ethyl-5-en-3-one, 4. This is isomerized using DBU to the 4-en-3-one, 5, which is oxidized to open Ring A to yield the seco-acid 6. This can be treated with amines, e.g. methylamine, to yield the A-ring closed 4-methyl-4-aza compound 7. This in turn can be catalytically hydrogenated to yield the 7-ethyl-5-alpha-4-methyl-4-aza-cholestan-3-one, 8.

Similarly, by treatment of the seco-acid 6 with ammonium acetate/acetic acid, the corresponding 4-NH analog 9, is produced which can be catalytically hydrogenated to yield the 7-beta-ethyl- 5α-4-aza-cholestan-3-one, 10.

Following the same procedure but using phenylmagnesium chloride as the Grignard reagent, the corresponding compounds 50 and 51 are produced.

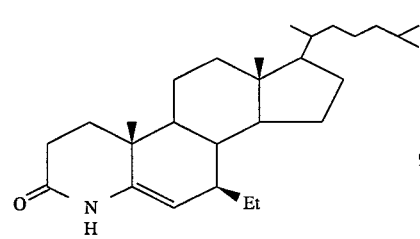

9

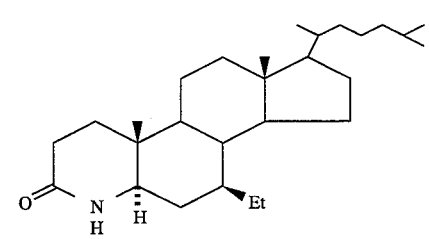

10

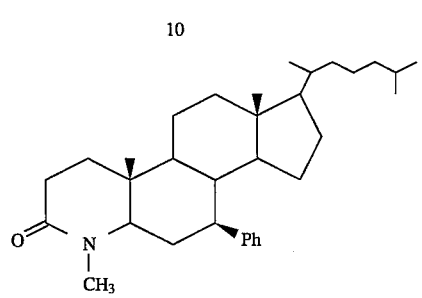

50

FLOWSHEET C

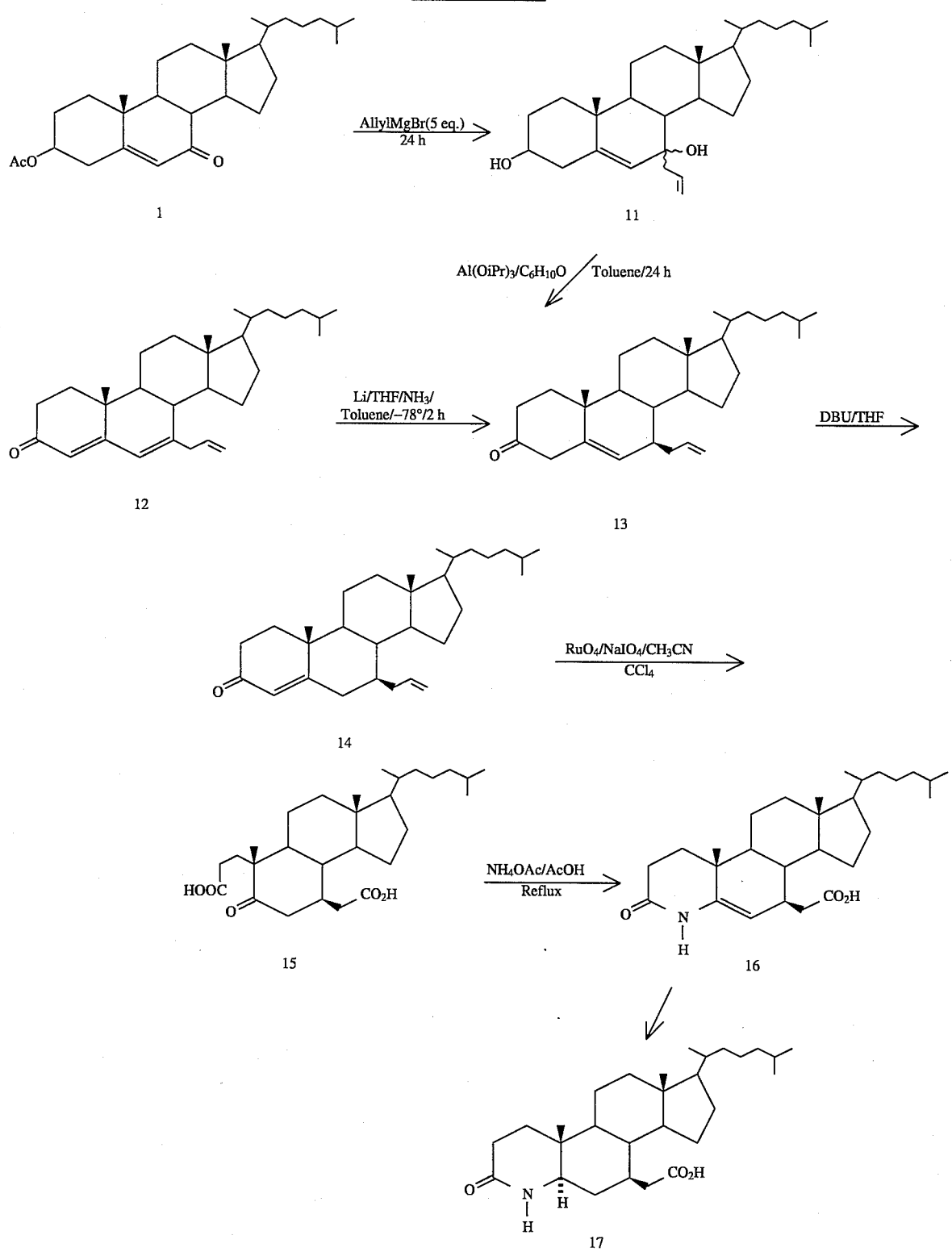

7-Carboxymethyl-Cholestane Series

The 7-carboxy substituent is formed through the corresponding 7-allyl group. As seen in Flowsheet C, 7-oxocholesteryl acetate 1 is reacted with allyl Grignard reagent to form the adduct 11 which is oxidized to the dienone 12 by Oppenauer conditions. Metal-ammonia reduction affords the 5-ene analog 13, followed by DBU-catalyzed double bond isomerization to 14. This in turn can be oxidized in a key step to form the 7-carboxymethyl seco-acid 15. Treatment with amines, e.g. ammonia, forms the 4-aza derivative, 16 which is then reduced to the cholestane 17. Use of methylamine in place of ammonia can yield the corresponding 4-methyl analogs of 16 and 17.
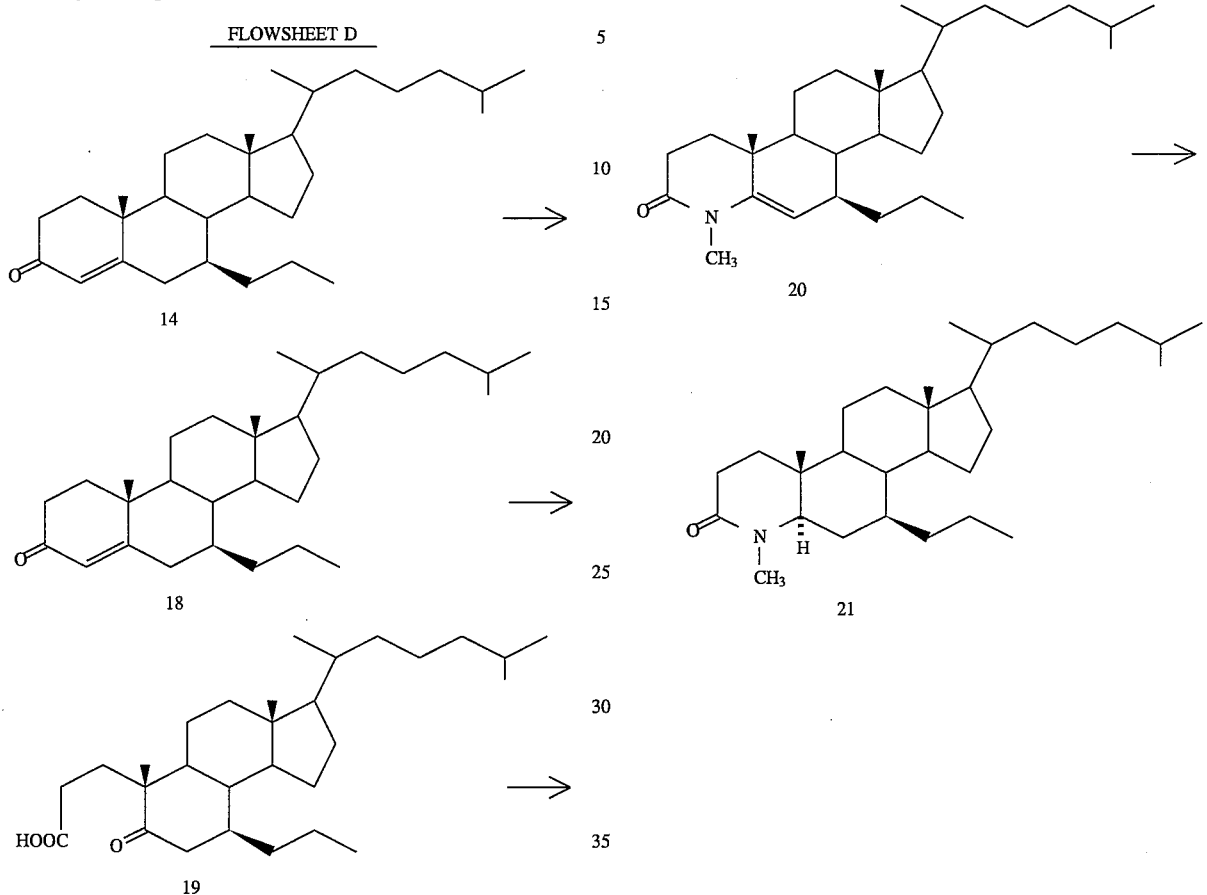
FLOWSHEET D
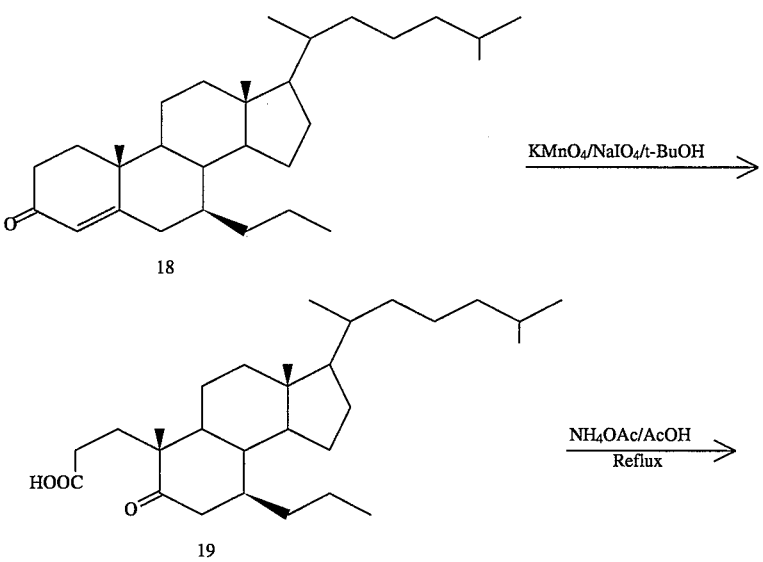
FLOWSHEET E -continued
FLOWSHEET E

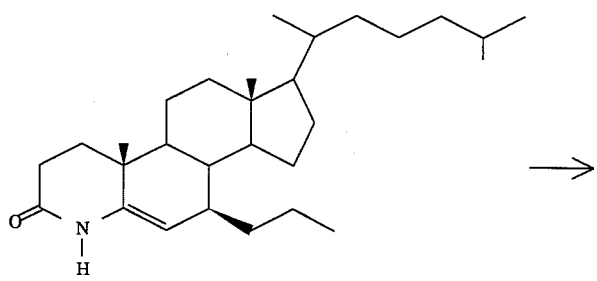

22

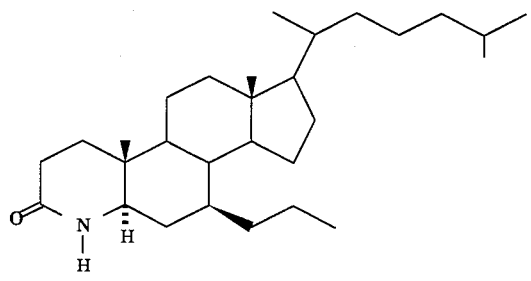

23

7-Propyl-Cholestane Series

The 7-propyl analogs are made starting with the 7-allyl-4-en-3-one 14, which is reduced by hydrogenation using Wilkinson's catalyst to the propyl derivative 18, oxidized to the seco-acid 19, then condensed with amines, e.g. methylamine, to form the 4-methyl analog 20 and then reduced to the cholestane 21. Corresponding treatment with ammonia is shown in Flowsheet E, which also shows the corresponding unsubstituted 4-aza 22 and cholestane 23 analogs.

FLOWSHEET F

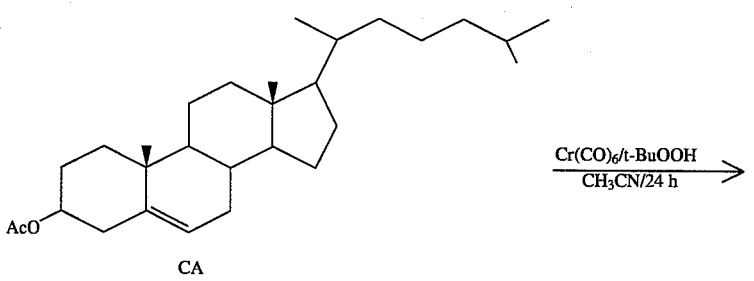

CA

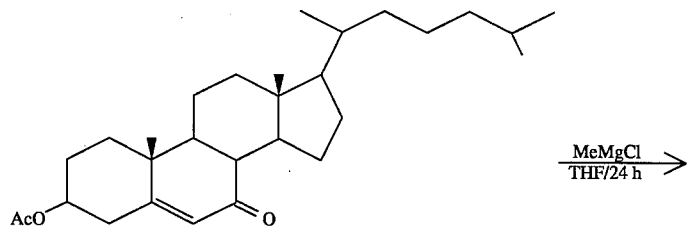

1

-continued
FLOWSHEET F
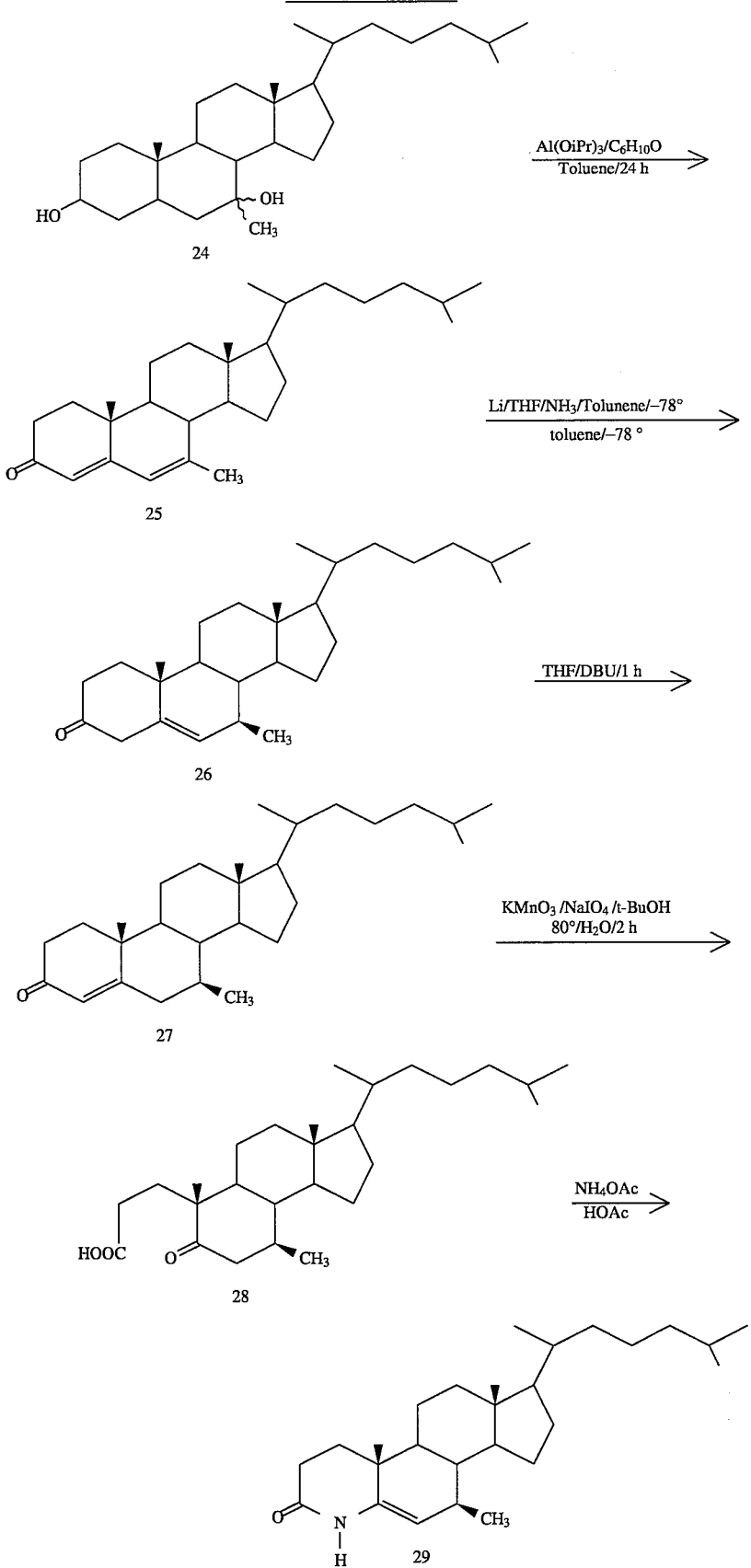

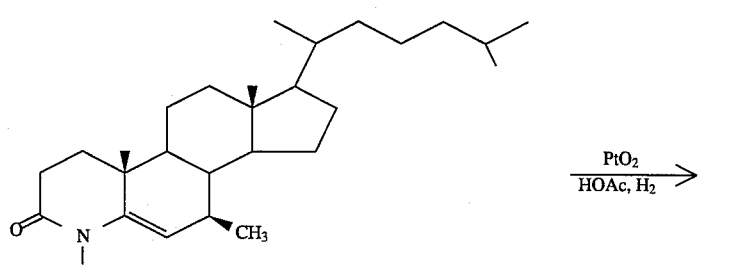

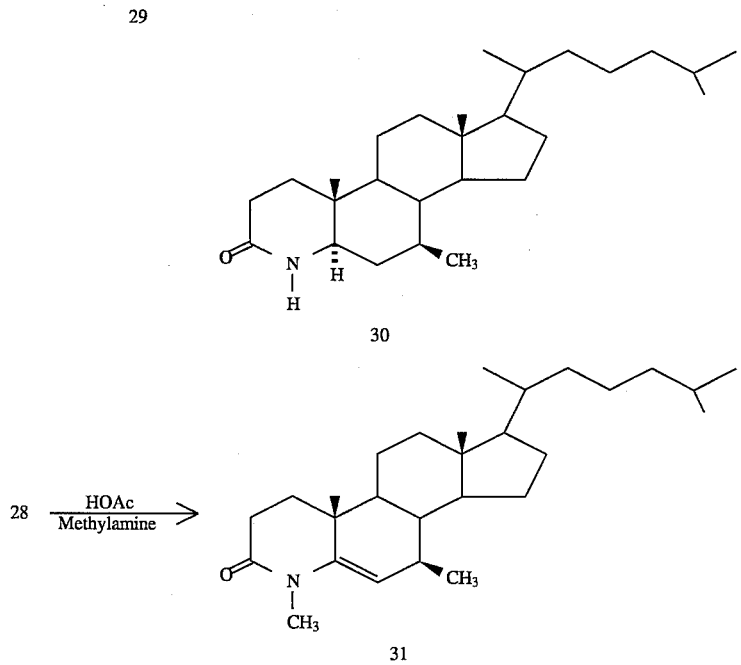

7-Beta Methyl Cholestane Series

The 7-beta methyl cholestane series is prepared by the analogously same route as described in Flowsheets A and B for the ethyl derivatives.

The methyl Grignard reagent is used to form the adduct 24, followed by Oppenauer oxidation to form 25, metal-ammonia reduction to form 26, double bond isomerization to form 27, seco-acid oxidation to form 28, and treatment by an ammonium salt to form 29, and reduction to form 30. Corresponding treatment with methylamine produces the corresponding 4-methyl-4-aza compounds, 31 and by reduction, 32.

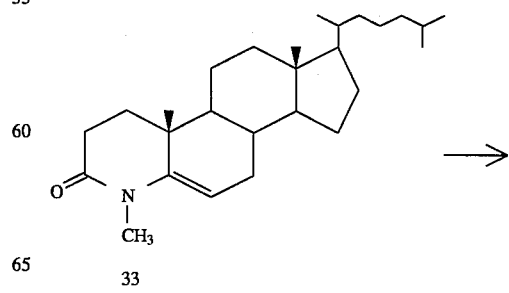

23
-continued
FLOWSHEET H

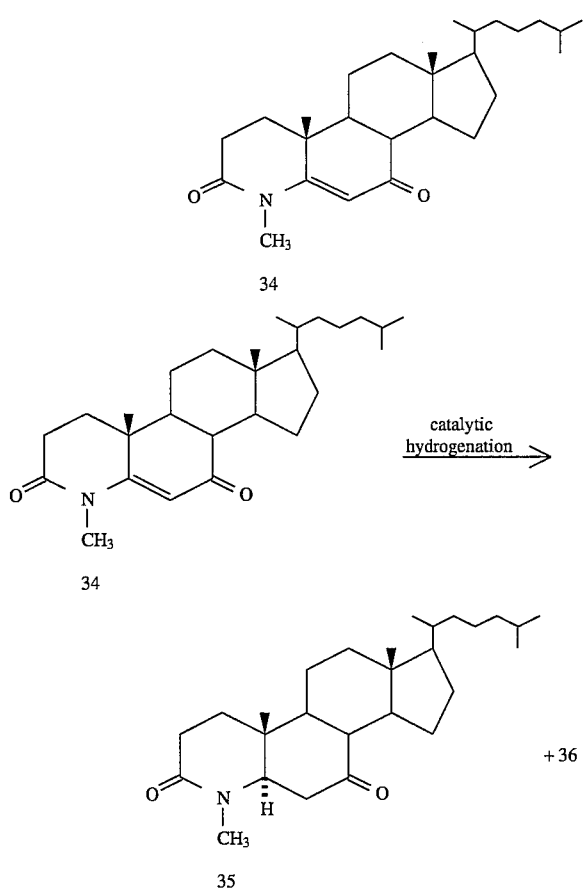

34

FLOWSHEET I

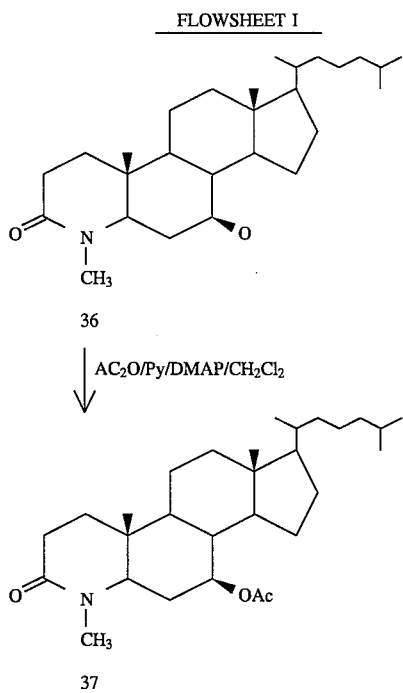

24

7-Beta Acetoxy Cholestane Series

The 7-beta acetoxy series is prepared by the oxidation of starting 33 to the 5-en-7-one 34 by the chromium hexacarbonyl procedure described for 1, or by pyridine-dichromate/t-butyl hydroperoxide oxidation as described in the Examples. Subsequent noble metal, e.g. platinum, ruthenium, catalyzed reduction of 34 yields two products, the reduced 7-oxo compound 35, and 7-beta hydroxy compound 36. Acylation of 36 with acetic anhydride yields the 7-beta acetoxy compound 37.

FLOWSHEET J

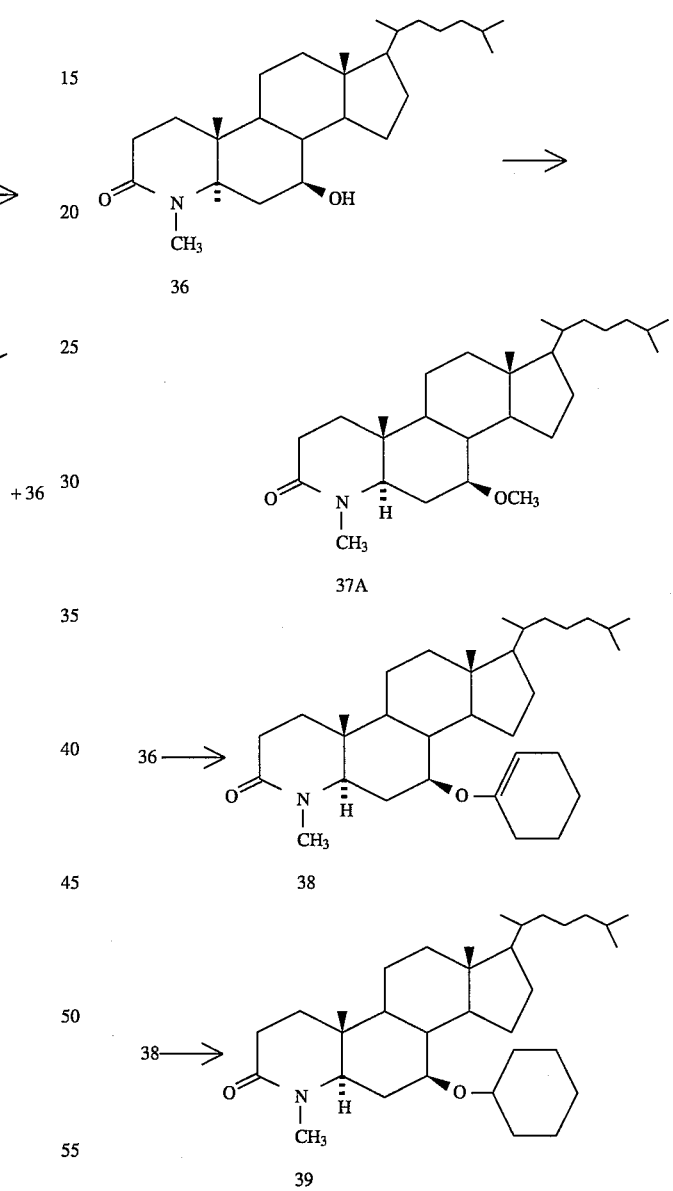

The 7-beta ethers in the cholestane series are prepared from the 7-beta-ol (7-beta hydroxy) derivative. As illustrated in Flowsheet J, the 4-N-methyl-7-beta ol 36 can be reacted with e.g. methyl iodide and sodium hydride in e.g., dimethylformamide, to produce the corresponding methyl ether 37A. The other $C_1$–$C_4$ ethers can be prepared in the same manner.

The $C_3$–$C_6$ cycloalkyl ethers can be prepared according to the analogous procedure of *Steroids*, 1972, vol. 19, pp. 639–647 by R. Gardi, et al. For example, 36 can be reacted with 1,1-dimethoxy-cyclohexane to produce the enol ether 38, which can be reduced to the corresponding saturated compound by the use of palladium catalyzed hydrogenation.
FLOWSHEET K
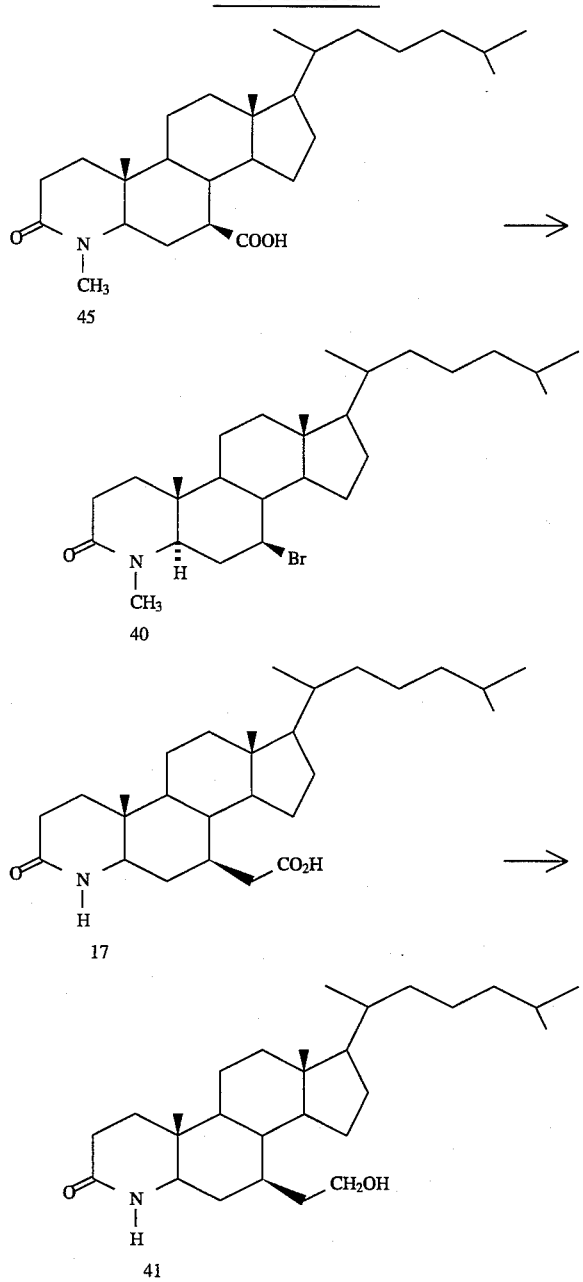
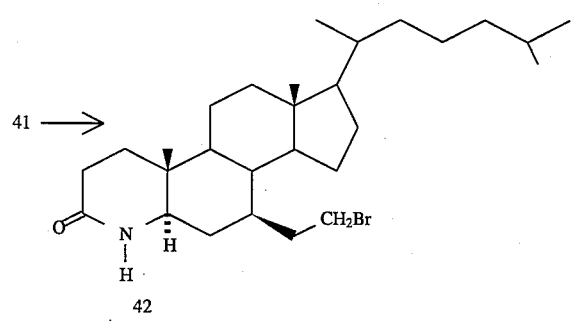
-continued
FLOWSHEET K
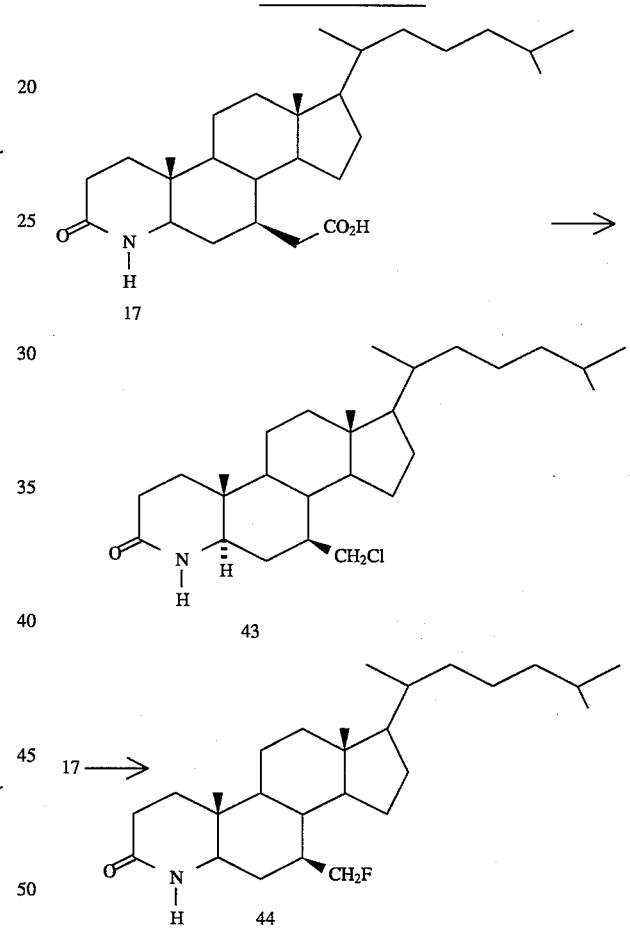
FLOWSHEET M
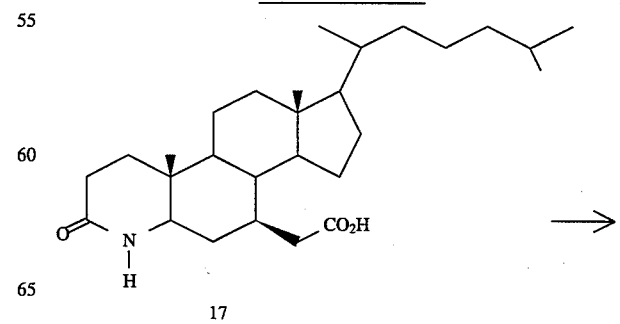

-continued
FLOWSHEET M

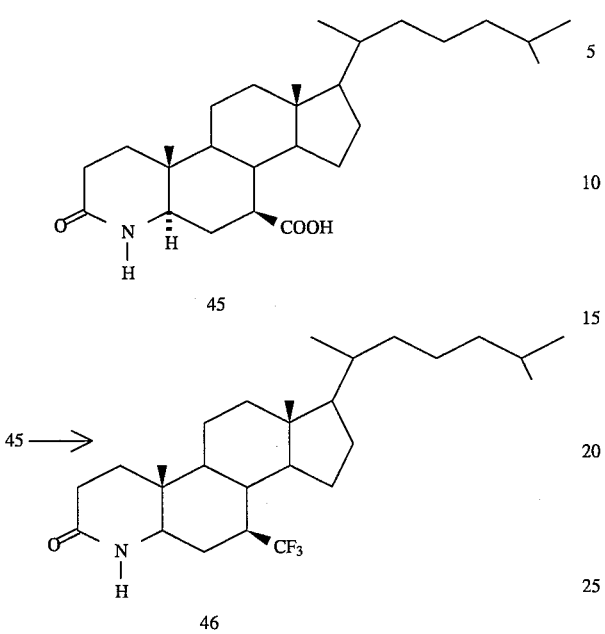

The 7-haloalkyl series is made by the procedure illustrated in Flowsheet K.

Starting with the 7-beta-carboxy, 45, this can be treated under Hunsdiecker reaction conditions, i.e. bromination of a mercury metal salt, to yield the 7-bromo derivative 40. The chloro and iodo derivatives can be made in substantially the same fashion.

The haloethyl compounds can be made by starting with the 7-carboxymethyl analog 17 which can be reacted with a reducing agent, e.g. borane, to produce the primary alcohol 41. This in turn can be reacted with triphenylphosphine and carbon tetrabromide to produce the bromoethyl derivative 42.

The halomethyl compounds can be produced starting with the carboxymethyl derivative 17. This is treated with lead tetraacetate under oxidative decarboxylation/halogenation conditions, with a chloride, bromide or iodide salt to yield, e.g. the 7-chloromethyl analog 43. The carboxymethyl compound 17 can be treated with a fluorinating agent (XeF$_2$) to yield the 7-fluoromethyl analog 44.

The 7-trifluoromethyl derivative can be made from the 7-carboxy derivative 45, by conventional Dast halogenation conditions using SF$_4$ to yield the 7-trifluoromethyl analog 46.

FLOWSHEET N

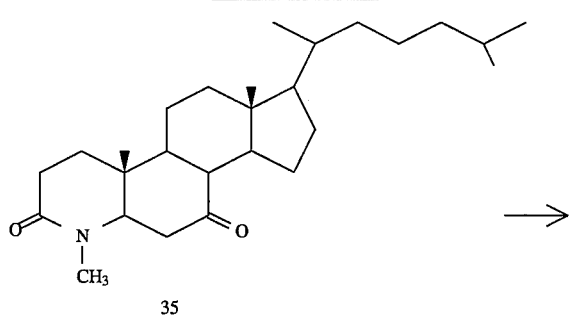

-continued
FLOWSHEET N

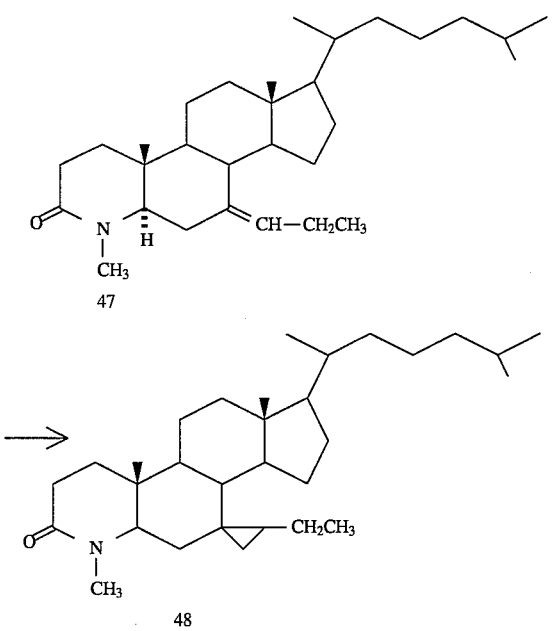

Flowsheet N illustrates the 7-methylene series. As seen, the Wittig reaction, using e.g. Ph$_3$PCH(CH$_2$CH$_3$), carried out on the 7-oxo compound 35, leads to the 7-(ethyl)methylene compound 47.

Subsequent treatment of 47 with the cyclopropyl forming reagents, CH$_2$I$_2$ and zinc, produces the ethyl cyclopropyl spiro compound 48, which is a mixture of stereoisomers.

FLOWSHEET O

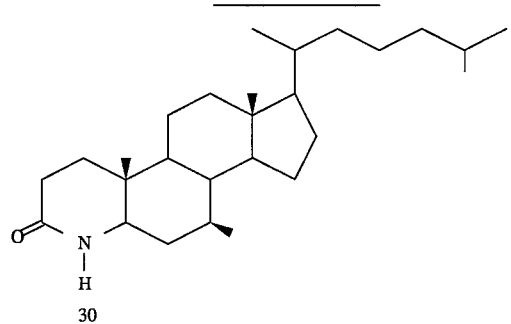

Flowsheet O illustrates the synthesis of the 1-ene 7-substituted analogs. For example compound 30 is stirred with DDQ, BSTFA (bis-trimethylsilyl-trifluoroacetamide) and trifluoromethyl sulfonic acid in toluene at room temperature for 24 hours, methyl acetoacetate is added and the mixture refluxed for 24 hours and purified by preparative thin layer chromatography on silica gel using 3:1 chloroform/acetone to yield 49.

Accordingly, the present invention is particularly concerned with providing a method of treating the hyperandrogenic conditions of andro-genic alopecia, acne vulgaris, seborrhea, and female hirsutism as well as benign prostatic hyperplasia, prostatitis, the prevention and/or treatment of prostatic carcinoma, by oral, parenteral or topical administration, of the novel compounds of the present invention.

The present invention is thus also concerned with providing suitable topical, oral and parenteral pharmaceutical formulations for use in the novel methods of treatment of the present invention.

The compositions containing the compounds of the present invention as the active ingredient for use in the treatment of e.g., benign prostatic hypertrophy, prostatitis, and prostatic carcinoma, and other hypo-androgenic conditions, can be administered in a wide variety of therapeutic dosage forms in conventional vehicles for systemic administration, as, for example, by oral administration in the form of tablets, capsules, solutions, or suspensions, of by injection. The daily dosage of the products may be varied over a wide range varying from 0.5 to 1,000 mg per adult human/per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calciuim phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservative are employed when intravenous administration is desired.

For the treatment of androgenic alopecia, acne vulgaris, seborrhea, female hirsutism, the compounds of the present invention are administered in a pharmaceutical composition comprising the active compound in combination with a pharmacologically acceptable carrier adapted for topical administration. Parenteral and oral administration is also applicable. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The following examples are illustrative of representative embodiments of this invention and should not be construed to be limits on the scope or spirit of the instant invention.

The Rf values cited were carried out on standard thin layer chromatographic Si gel plates. The elution solvent system used is given in the parentheses following the Rf value.

The mass spectral values are given either as FAB, i.e., fast atom bombardment, and are reported as (M+1) molecular ion peaks, being the molecular weight plus one atomic mass unit. The electron impact (EI) mass spectrum values are reported as molecular ion peaks and are indicated in parentheses, either being (M) or (M+2), the molecular weight, MW, or the MW plus two atomic units.

The nuclear magnetic resonance data was taken at 400 MHz in $CDCl_3$ and is tabulated for unique proton values of each compound at the end of the Examples. The coupling constant 3 is given in Hertz, Hz.

EXAMPLE 1

Synthesis of 7-Oxo-Cholesterol-3-acetate (1).

Cholesteryl acetate (CA) is known in the art and can be oxidized to the known 7-oxo-derivative 1 by the analogous procedure described in the JCS Perkins article by Pearson, supra.

EXAMPLE 2

Synthesis of 7-Ethyl-7-Hydroxy-cholesterol, (2)

To a solution of 1 from Example 1, being 5.0 g (11.32 mmol) in dry tetrahydrofuran at 0° C. was added dropwise 56.6 ml ethyl magnesium bromide (1M) over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield a yellowish-white foam. The Rf value was 0.2 (30% EtOAc/hexane). Proton NMR confirmed the assigned structure of the title compound 2 which was used in the next step without further purification.

EXAMPLE 3

Synthesis of 7-Ethyl-Cholest-4,6-Dien-3-one, (3)

The above Grignard product 2, 5.13 g (11.9 mmol) was dissolved in 50 ml toluene and cyclohexanone and about 40 ml of solvent distilled off under vacuum. To this was added 7.2 g aluminum isopropoxide and the reaction mixture refluxed overnight for 15 hours. The mixture was cooled, diluted with ethyl acetate, washed with sodium potassium tartarate, brine, and the organic layer was concentrated under vacuum and the residue steam distilled. The residue was extracted with ethyl acetate, the ethyl acetate layer, washed with brine, dried and purified by column chromatography on silica gel, eluting with 5% EtOAc/hexane to yield the title compound 3. Rf=0.58 (20% EtOAc/hexane). Mass spec: 412(M=1) by FAB, Calc'd. 411.9.

EXAMPLE 4

Synthesis of 7β-ethyl-cholest-5-en-3-one, (4)

To a solution of 3.1 g of 3, from Example 3, in 46 ml ammonia, 10 ml THF, 10 milliliters toluene, was added 449 mg of metallic lithium in small pieces. After stirring the blue solution for 2 hours at −78° C., a solution of 1,2-dibromoethane in 2 ml THF was added. After stirring the solution at −78° C. for 10 minutes, 2.1 g of ammonium chloride was added and the mixture stirred for 10 minutes. The excess ammonia was removed by evaporation under a nitrogen stream. The reaction mixture was diluted with brine, extracted with ethyl acetate. The organic layer was washed with brine, dried and concentrated to yield crude brown viscous liquid 4 which was used as such in Example 5. Rf=0.70 (20% EtOAc/hexane). Mass Spec. 412 (EI); calculated MW 412.70.

EXAMPLE 5

Synthesis of 7β-ethyl-cholest-4-en-3-one (5).

To a solution of 4, from Example 4, being 3.1 g in 30 ml THF was added 1.1 ml DBU (1,8-diazabicyclo[5.4,0]undec-7-ene under nitrogen with stirring. The mixture was refluxed for 1.5 hours, then cooled and diluted with NH4Cl. Then THF solvent was removed under vacuum and the residue extracted with ethyl acetate. The organic layer was then washed with water, brine, dried and concentrated under reduced pressure to yield a crude viscous oil. The titled product 5 was purified by chromatography on silica gel using 10% EtOAc/hexane as eluant. Mass Spec 412 (EI), calc'd MW 412.70. Rf=0.6 (20% EtOAc/hexane).

EXAMPLE 6

Synthesis of 7-ethyl-17β-(6-methyl-2-heptyl)- 5-oxo-A-nor-3.5-secoandrostan-3-oic acid, (6)

To a solution of 1.0 g of 5 in 18 ml t-butyl alcohol at 80° C. was added 300 mg sodium carbonate in 1.8 ml water followed by a dropwise addition over 15–20 minutes of a mixture of 2.74 g sodium periodate with 20.3 mg potassium permanganate in 15 ml water. The reaction mixture was heated at 80° C. for 2 hours, cooled, filtered, the residue washed with water, and then the filtrate concentrated under vacuum, acidified with aqueous HCl, extracted with ethyl acetate and the organic layer washed with aqueous NaHSO$_3$, brine, dried and concentrated to yield crude 6. The proton NMR confirmed the assigned structure. Fast atom bombardment yielded an m/z molecular ion of 434(m+2 ); calculated 432.69.

EXAMPLE 7

Synthesis of 7-Ethyl-4-methyl-4-aza-cholest-5-en-3-one, (7)

To a solution of 6, 500 mg in 10 ml ethylene glycol was added 1.3 g sodium acetate and 1.0 g methylamine hydrochloride. After stirring the reaction mixture 4 hours at 180° C., the mixture was cooled, diluted with water, extracted with ethyl acetate, dried and concentrated to afford crude title compound 7. Proton NMR confirmed the assigned structure. Rf=0.70 (20% EtOAc/hexane).

Mass Spectral m/z ion (FAB) showed 429 (M+2). calculated, 427.72.

Analysis: Calc. for $C_{29}H_{49}NO$ Calc.: C; 81.44; H, 11.55; N, 3.27 Found: C, 82.19; H, 10.92; N, 3.11.

EXAMPLE 8

Synthesis of 7-Ethyl-4-methyl-4-Aza-Cholestan-3-one, (8)

To a solution of 7 from Example 7, being 180 mg in 5 ml acetic acid was added 54 mg platinum dioxide and the resulting mixture was evacuated and flushed with hydrogen. The reaction was shaken overnight at room temperature under hydrogen. Filtered, washed solid with EtOAc, combined EtOAc layers were washed with aqueous NaHCO$_3$, brine, dried, concentrated to yield the title compound 8.

Mass spectral analysis by FAB yielded m/z ion of 431 (m+2), calculated 429.74.

Analysis for $C_{29}H_{51}NO$ Calc: C, 81.06; H, 11.96, N, 3.26 Found: C, 81.42; H, 12.24; N, 3.16

EXAMPLE 9

Synthesis of 7-Ethyl-4-Aza-Cholest-5-en-3-one, (9)

The seco acid 6, 0.5 g. and ammonium acetate, 0.5 g., in 3.5 ml acetic acid were refluxed for 3 hours. The reaction mixture was cooled, water added and then extracted with ethyl acetate. The organic layer was dried over sodium sulfate and concentrated to yield a residue which was eluted on a silica gel column with 10% EtOAc/hexane to give pure title compound 9, mp. 147°–149° C.

Mass Spec. 414 (Mtl). Calc'd; 413.69. Rf=0.45 (30% EtOAc/hexane).

Analysis for $C_{28}H_{49}NO$, MW 413.69 Calc.: C, 81.30; H, 11.45; N, 3.39 Found: C, 81.30; H, 11.87; N, 3.45

EXAMPLE 10

Synthesis of 7β-Ethyl-4-aza-5α-cholestan-3-one, (10)

Following the general analogous procedure described in Example 8, 9 was catalytically hydrogenated to yield the titled compound, 10. Chromatography on silica gel with 50% EtOAc:hexane eluant yielded pure product, mp. 169°–170° C.

Analysis for $C_{28}H_{49}NO$, MW=415.17. Calcd: C; 80.90; H, 11.88; N, 3.37 Found: C; 81.02; H, 12.57; N, 3.47.

Mass Spec.: 416 (M+1) Rf=0.30 (30% EtOAc/hexane)

EXAMPLE 11

Synthesis of 7-Allyl-3,7-dihydroxy-cholest-5-ene (11)

Following the analogous general Grignard procedure of Example 2, allyl magnesium bromide was reacted with Compound 1 in dry THF to yield the titled product 11. Proton NMR confirmed the assigned structure.

Mass Spec. 441 (M+1). Calc'd. 440.71. Rf=0.25 (30% EtOAc/hexane).

EXAMPLE 12

Synthesis of 7-allyl-cholest-4,6-dien-3-one, (12)

Following the analogous general Oppenauer oxidation procedure of Example 3, compound 11 was oxidized to yield the titled compound 12. Proton NMR confirmed the assigned structure as well the (FAB) mass spec. 423 (M+1) Calc'd. 422.35. Rf=0.78 (30% EtOAc/hexane).

EXAMPLE 13

Synthesis of 7-Allyl-cholest-5-en-3-one, (13)

Compound 12, was subjected to the analogous metal-ammonia reduction conditions of Example 4 to yield the title compound 13. Rf=0.5 (5% EtOAc/hexane).

EXAMPLE 14

Synthesis of 7-Allyl-cholest-4-en-3-one, (14)

Following the general DBU catalyzed isomerization conditions of Example 5, compound 13 was analogously treated to yield the title compound 14.

Mass Spec. 425 (M+1) by FAB. Calc'd.: 424.37 Rf=0.45 (5% EtOAc/hexane).

EXAMPLE 15

Synthesis of 7-Propyl-cholest-4-en-3-one, (18)

1.0 g. of the 7-allyl-enone 14, 5 ml. EtOAc and 50 mg. triphenylphosphine rhodium chloride (Wilkinson's catalyst) were allowed to stir two hours (under H$_2$ atmosphere). The reaction products were filtered through 25 ml. silica gel, and evaporated to dryness to yield fairly pure title product, 18, as confirmed by proton NMR.

Mass Spec. 427 (M+1). Calc'd.: 426.39 Rf=0.15 (5% EtOAc/hexane).

EXAMPLE 16

Synthesis of 7-Propyl-5-oxo-A-nor-3,5-seco-cholestanoic acid, (19)

Following the general procedure of Example 6 for the oxidative Ring A cleavage, compound 18 (7-propyl analogue) was analogously treated to yield the above-titled seco-acid 19. The assigned structure was confirmed by proton NMR. Mass Spec.: 447 (M+1) (FAB). Calc'd.: 446.38 Rf=0.1 (20% EtOAc/hexane).

EXAMPLE 17

Synthesis of 7-Propyl-4-methyl-4-aza-cholest-5-en-3-one, (20)

Following the general procedure of Example 7, compound 19, was analogously treated with methylamine hydrochloride and sodium acetate in ethylene glycol to yield the above-titled liquid product 20 The assigned structure was confirmed by proton NMR.

Mass Spec. 442 (M+1) (FAB), Calc'd.: 441.74 C,H,N analysis for C H N O as 0.2 $H_2O$, MW=441.74; Calcd: C, 80.91; H, 11.63; N, 3.15. Found: C, 81.00; H, 12.06; N, 2.93. Rf=0.3 (20% EtOAc/hexane).

EXAMPLE 18

Synthesis of 7-Propyl-4-methyl-4-aza-5α-cholestan-3-one, (21)

Following the analogous general procedure of Example 8, compound 20 was catalytically hydrogenated in HOAc to yield the title liquid compound 21. Proton NMR confirmed the assigned structure.

Mass spec. 444 (M+1) (FAB), C,H,N analysis for C H N; Calcd: C, 81.19; H, 12.05; N, 3.16. MW=443.41. Found: C, 80.78; H, 12.06; N, 3.22.

Rf=0.17 (20% EtOAc/hexane).

EXAMPLE 19

Synthesis of 7-Propyl-4-aza-cholest-5-en-3-one, (22)

Following the analogous procedure of Example 9, compound 19 was treated with ammonium acetate in acetic acid to yield the titled compound, 22. Recrystallized from EtOAc/$Et_2O$ to yield a white crystalline solid, mp. 91°–94° C., C,H,N analysis as the 0.25 $H_2O$ hydrate: Calc'd MW 427.39 Calcd: C, 80.59; H, 11.54; N, 3.24. Found: C, 80.59; H, 11.69; N, 3.36.

Mass Spec. 428 (M+1).

EXAMPLE 20

Synthesis of 7-Propyl-4-aza-5α-cholestan-3-one, (23)

Following the analogous procedure described in Example 8, compound 22 was catalytically hydrogenated to yield the title compound 23, mp. 65°–68° C.

Analysis for C,H,N, calc'd as 0.25 $H_2O$ hydrate: Calcd: C, 80.21; H, 11.95; N, 3.23. Found: C, 80.20; H, 12.14; N, 3.07. Proton nmr Mass Spec.=430 (M+1) calc'd MW 429.40.

Rf=0.12 (20% EtOAc/hexane).

EXAMPLE 21

Synthesis of 7-Methyl-7-Hydroxy-cholesterol, (24)

Following the analogous Grignard procedure of Example 1, cholesteryl acetate-7-one 1 was reacted with methyl magnesium bromide under standard Grignard conditions to yield title compound 24, a solid. NMR confirmed the assigned structure and mass spectral analysis confirmed the molecular weight.

EXAMPLE 22

Synthesis of 7-Methyl-Cholest-4,6-Dien-3-one, (25)

Following the analogous procedure of Example 2, the above Grignard product 24, was subjected to Oppenauer oxidation conditions to yield the title compound, 7β-methyl-cholest-4,6-dien-3-one, 25.

EXAMPLE 23

Synthesis of 7β-methyl-cholest-5-en-3-one, (26)

Following the analogous procedure of Example 4 for the metal-ammonia reduction, 25 was similarly treated with lithium in ammonia/THF/toluene to yield title compound 2.6.

EXAMPLE 24

Synthesis of 7β-methyl-cholest-4-en-3-one (27)

Following the general isomerization procedure of Example 5 using DBU in THF, 26 was analogously treated to yield the title compound 27.

EXAMPLE 25

Synthesis of 7-methyl-17β-(2,6-Dimethylhexyl)-5-oxo-A-nor- 3,5-secoandrostan-3-oic acid, (28)

Following the general procedure of Example 6 for the oxidative Ring A cleavage, compound 27 was analogous treated to yield the above titled seco-acid 28. The proton NMR confirmed the assigned structure.

EXAMPLE 26

Synthesis of 7-Methyl-4-aza-cholest-5-en-3-one, (29)

Following the general procedure of Example 9, compound 28 was analogously treated with ammonium chloride in acetic acid to yield the above-titled product 29.

Mass Spectral m/z ion (FB) showed 400.2 (M+1) (M+2).calculated, 399.

EXAMPLE 27

Synthesis of 7-Methyl-4-aza-Cholestan-3-one, (30)

Following the analogous general procedure of Example 8, compound 29 was catalytically hydrogenated in HOAc to yield the title compound 30.

Mass spectral analysis by EI yielded m/z ion of 401 calculated 401.

EXAMPLE 28

Synthesis of 7-Methyl-4-methyl-4-Aza-Cholest-5-en-3-one, (31)

The seco acid 28, was treated analogously as in Example 7 to give pure title compound 31.

Mass Spec. 414 (m+1) by FAB, calc'd., 413.

EXAMPLE 29

Synthesis of 7β-Methyl-4-methyl-4-aza-5α-cholestan-3-one, (32)

Following the general analogous procedure described in Example 8, 31 was catalytically hydrogenated to yield the titled compound, 32. Chromatography on silica gel with 30% EtOAc/hexane, eluant yielded pure product.

Mass Spec. (EI) 415, calc'd., 415.

EXAMPLE 30

Synthesis of 4-methyl-4-aza-cholest-5-en-3,7-dione, (34)

An oxidation procedure is carried out on 4-methyl-4-aza-cholest-5-en-3-one 33 to yield the title compound, 34. (See U.S. Pat. No. 3,264,301 by Doorenboos and J. Org. Chem. 1961, Vol. 26, p.4548.) The compound 33 was heated at 70° C. with a mixture of pyridinium dichromate/t-butyl hydroperoxide in benzene over a 3–4 hour period to produce 34.

EXAMPLE 31

Synthesis of 7β-Acetoxy-4-methyl-4-aza-5α-cholestan-3-one (37)

Compound 34 is hydrogenated by the analogous procedure of Example 8 to produce the 7-H analog 35, and the 7β-ol, 36. Acylation of 36 with acetic anhydride, in the presence of pyridine, 4-dimethylaminopyridine in methylene chloride at 23° C. for 24 hrs. produces the title compound 37.

EXAMPLE 32

Synthesis of 7-Beta Methyl-4-aza-5α-cholest-1-en-3-one (49)

To a solution of 280 mg, (0.698 mmol) of 30 in 4 milliliters toluene, was added 178.8 mg. DDQ, 0.7186 mg. BSTFA and 8.163 mg. triflic acid and the reaction contents allowed to stir at room temperature for 24 hours. Methyl acetoacetate, 8.1 mg., was added and the reaction refluxed for 24 hours. The contents were cooled, diluted with ethyl acetate, washed with aqueous sodium carbonate, aqueous sodium bisulfite, brine, dried over magnesium sulfate and concentrated to yield an oil. The crude compound was purified by preparative TLC on silica gel, eluting with 3:1CHCl₃/acetone to yield pure 49, whose proton NMR confirmed the assigned structure.

The following Table lists the unique proton NMR values (400 MHz in CDCl₃) for each compound. The data are reported as: s=singlet, d=doublet, m=multiplet, J=coupling constant. The absorption values are given del (δ) units and are illustrated for the C-18, C-19 and C-21 angular ring methyl protons and protons associated with unique portions of the molecule.

The numbering of the 4-aza steroid is given by the following structure;

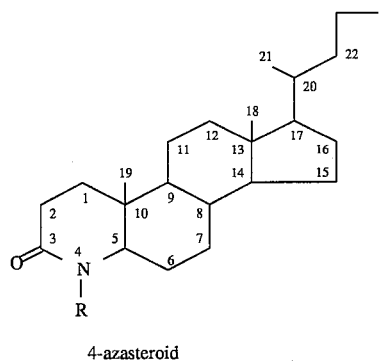

4-azasteroid

TABLE

| Compound No. | 18-CH₃ | 19-CH₃ | 21-CH₃ | Others |
|---|---|---|---|---|
| 2 | s 0.660 0.662 | s 1.030 1.060 | d 0.940 J=7 | 6H s 6.120 (values given for second isomer) |
| 3 | s 0.755 | s 1.061 | d 0.915 J=7 | 4H and 6H s 5.61, 5.97 |
| 4 | s 0.720 | s 1.110 | d 0.930 J=7 | 4 CH₂ m 2.83–3.28 |
| 5 | s 0.730 | s 1.12 | d 0.930 J=7 | 4H s 5.74 |
| 6 | s 0.66 | s 0.963 | d 0.894 J=7 | |
| 7 | s 0.692 | s 0.977 | d 0.908 J=7 | N—CH₃ s 3.153 |
| 8 | s 0.690 | s 0.830 | d 0.900 J=7 | N—CH₃ s 2.93 |
| 9 | s 0.653 | s 0.991 | d 0.903 J=7 | 6H d 4.91 J=4 |
| 10 | s 0.675 | s 0.808 | d 0.893 J=7 | 5H, m, 2.97–3.13 |
| 11 | s 0.66 | s 0.90 | d 0.915 J=7 | allylic H m (5.8–5.94) |
| 12 | s 0.78 | s 1.07 | d 0.96 J=7 | allylic H m (5.73–5.85) |
| 13 | s 0.70 | s 1.08 | d 0.90 J=7 | 6H, s (5.23) |
| 14 | s 0.73 | s 1.13 | d 0.93 J=7 | 4H s 5.72 |
| 18 | s 0.71 | s 1.13 | d 0.93 J=7 | 4H s 5.71 |
| 19 | s 0.65 | s 0.963 | d 0.91 J=7 | |
| 20 | s 0.691 | s 0.974 | d 0.902 J=7 | (6H) - d 4.92d, (J=4) (N—CH₃) s 3.16 |
| 21 | s 0.665 | s 0.795 | d 0.883 J=7 | (N—CH₃) s 2.92 5H m (2.96–3.00) |
| 22 | s 0.680 | s 1.01 | d 0.890 J=7 | (6H) d 4.86 J=4 |
| 23 | s 0.680 | s 0.808 | d 0.884 J=7 | 5H m (3.0–3.1) |
| 24 | s, 0.680, 0.69 | s, 0.94, 1.04 | d 0.91 J=7 | 6H, s, 5.19, 5.21 |
| 25 | s, 0.76 | s, 1.07 | d 0.92 J=7 | 4H, 6H 5.59, 5.92 |

TABLE-continued

| Compound No. | 18-CH₃ | 19-CH₃ | 21-CH₃ | Others |
|---|---|---|---|---|
| 27 | s, 0.70 | s, 1.15 | d 0.92 J=7 | 7-CH₃, d, 1.04, J=6.5 4H, s, 5.71 |
| 28 | s, 0.69 | s, 1.12 | d 0.92 J=7 | 7-CH₃, d, 0.96, J=6.5 |
| 29 | s, 0.69 | s, 1.04 | d 0.91 J=7 | 7-CH₃, d, 0.97, J=6.5 6H, d, 4.59, J=3.0 |
| 30 | s, 0.67 | s, 0.835 | d 0.91 J=7 | 7-CH₃, d, 1.00, J=6.5 5H, dd, J=3.3, 12.63 |
| 31 | s, 0.69 | s, 1.00 | d 0.95 J=7 | 7-CH₃, d, 1.05, J=6.5 6H, d, J=3.0 |
| 32 | s, 0.68 | s, 0.825 | d 0.91, J=7H | 7-CH₃, d, 1.05, J=6.5 4-CH₃, s, 3.92 |
| 33 | s, 0.69 | s, 1.23 | d 0.91 J=7 | C6 - s, 5.42 N-CH₃, s, 3.14 Mass-Spec (EI)=413 |
| 49 | s, 0.69 | s, 0.90 | d 0.915 J=7 | C-7CH₃, 1.02, d, J=6, C-2, 1H, 5.79, dd J=2.5 J=9.1 |
| 50 | s, 0.62 | s, 1.01 | d 0.86 J=7 | C-5, 1E, 3.08, dd J=3.87 J=12.9 C-7Ph, 5H, m, 7.1–7.3 |
| 51 | s, 0.63 | s, 1.02 | d 0.8 J=7 | C-5, 1-H, 3.2, dd J=5.88 J=10.5 C-7Ph, 5H, m, 7.08–7.3 |

What is claimed is:

1. A compound of the formula:

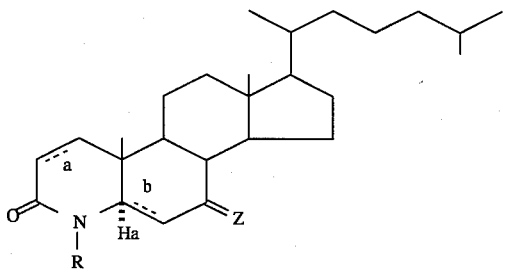

wherein:

R is selected from hydrogen, methyl, ethyl, —OH, —NH₂, and —SCH₃; the dashed lines a and b indicate double bonds which can be present providing that when b is present, the 5α hydrogen, Ha, is absent;

Z is:

1) oxo,

2) α-hydrogen and a β-substituent selected from: $C_1$–$C_4$ alkyl, $C_2$–$C_4$ alkenyl, CH₂COOH, hydroxy, carboxy, —COO$C_1$–$C_4$ alkyl esters; —OCONR¹R² where R¹ and R² are independently H, $C_1$–$C_4$ alkyl, phenyl, and benzyl; O$C_1$–$C_4$ alkyl, O$C_3$–$C_6$ cycloalkyl, —OCOCH3, halo, hydroxy-$C_1$–$C_2$ alkyl, halo-$C_1$–$C_2$ alkyl or trifluoromethyl; $C_3$–$C_6$ cycloalkyl;

3) =CH—R' where R' is —H, $C_1$–$C_4$ alkyl;

4) spiro:

where R' is H, $C_1$–$C_4$ alkyl;

and stereoisomers and pharmaceutically acceptable salts thereof.

2. A compound of claim 1 wherein double bond a is absent and is of the structure:

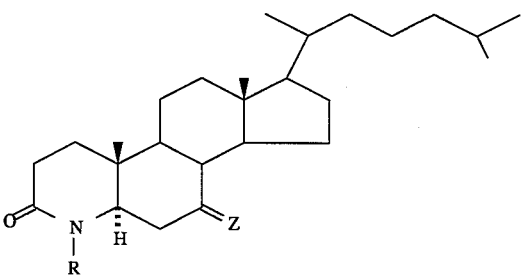

3. The compound of claim 1 wherein double bond a is absent and is of the structure:

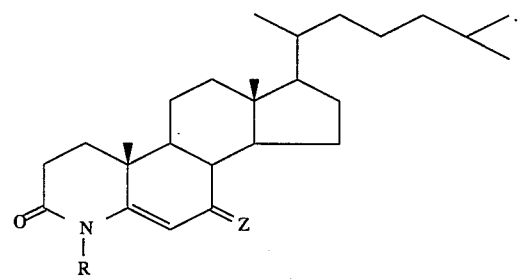

4. The compound of claim 1 wherein double bond a is absent and R is methyl and is of the structure:

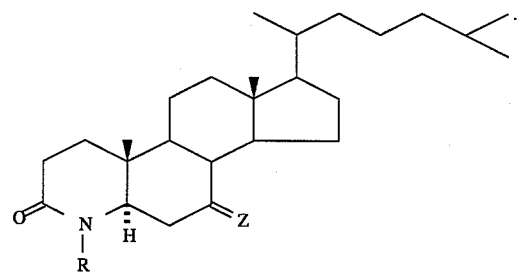

5. The compound of claim 1 wherein double bond a is present and is of the structure:

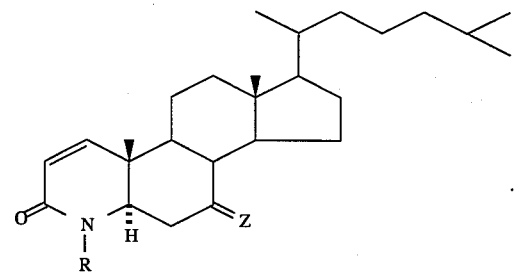

6. The compound of claim 1 wherein Z is α-hydrogen and the β-substituent is $C_1$–$C_4$alkyl, or $C_2$–$C_4$alkenyl.

7. The compound of claim 1 selected from the group consisting of:
7β-ethyl-4-methyl-4-aza-cholest-5-en-3-one,
7β-ethyl-4-methyl-4-aza-cholestane-3-one,
7β-ethyl-4-aza-cholest-5-en-3-one,
7β-ethyl-4-aza-5α-cholestan-3-one,
7β-carboxymethyl-4-aza-cholest-5-en-3-one,
7β-carboxymethyl-4-aza-cholestan-3-one,
7β-propyl-4-methyl-4-aza-cholest-5-en-3-one,
7β-propyl-4-methyl-4-aza-5α-cholestan-3-one,
7β-propyl-4-aza-cholest-5-en-3-one,
7β-propyl-4-aza-5α-cholestan-3-one,
7β-methyl-4-aza-cholest-5-en-3-one,
7β-methyl-4-aza-cholestan-3-one,
4,7β-dimethyl-4-aza-cholest-5-en-3-one,
4,7β-dimethyl-4-aza-5α-cholestan-3-one,
7β-acetoxy-4-methyl-4-aza-5α-cholestan-3-one,
4-methyl-4-aza-cholest-5-en-3,7-dione,
7β-hydroxy-4-methyl-4-aza-5α-cholestane-3-one,
7β-methoxy-4-methyl-4-aza-5α-cholestane-3-one,
7β-hydroxymethyl-4-aza-5α-cholestane-3-one,
7β-bromomethyl-4-aza-5α-cholestane-3-one,
7β-chloromethyl-4-aza-5α-cholestane-3-one,
7β-fluoromethyl-4-aza-5α-cholestane-3-one,
7β-carboxy-4-aza-5α-cholestane-3-one,
7β-trifluoromethyl-4-aza-cholest-5-en-3-one,
4-methyl-4-aza-cholesta-3,7-dione,
7,7-dimethoxy-4-methyl-4-aza-5α-cholestane-3-one
7β-methoxy-4-methyl-4-aza-5α-cholestane-3-one,
7β-cyclopropyloxy-4-methyl-4-aza-5α-cholestane-3-one,
7β-(ethyl)exomethylene-4-methyl-4-aza-5α-cholestane-3-one,
7β-(2-ethyl)-cyclopropyl-4-methyl-4-aza-5α-cholestane-3-one, and
7β-(2-ethyl)-spiroethylene-4-methyl-4-aza-5α-cholestane-3-one.

8. A pharmaceutical composition consisting essentially of 0.5 to 1000 mg of a compound of claim 1 in a pharmaceutically acceptable carrier therefor.

* * * * *